United States Patent
Linders et al.

(10) Patent No.: US 11,857,303 B2
(45) Date of Patent: Jan. 2, 2024

(54) APPARATUS AND METHOD OF MEASURING BLOOD FLOW IN THE FOOT

(71) Applicant: Podimetrics, Inc., Somerville, MA (US)

(72) Inventors: David Linders, Carnation, WA (US); Zoe Wolszon, Austin, TX (US); Jacob O'Brien, Cambridge, MA (US); Madeline Diane Rogers, Collegeville, PA (US); Lauren O'Neil Grove, Barrington, RI (US); Dennis Lan-Bo Wei, Attleboro, MA (US); Emma Grace Lloyd, Salem, MA (US); Heather Gerstley, Woodcliff Lake, NJ (US); Benjamin Thomas Centracchio, Essex, VT (US)

(73) Assignee: Podimetrics, Inc., Somerville, MA (US)

(*) Notice: Subject to any disclaimer, the term of this patent is extended or adjusted under 35 U.S.C. 154(b) by 0 days.

(21) Appl. No.: 18/076,038

(22) Filed: Dec. 6, 2022

(65) Prior Publication Data

US 2023/0172471 A1 Jun. 8, 2023

Related U.S. Application Data

(60) Provisional application No. 63/286,352, filed on Dec. 6, 2021.

(51) Int. Cl.
*A61B 5/0295* (2006.01)
*A61B 5/00* (2006.01)

(52) U.S. Cl.
CPC .......... *A61B 5/0295* (2013.01); *A61B 5/7203* (2013.01)

(58) Field of Classification Search
CPC ... A61B 5/0295; A61B 5/7203; A61B 5/0261; A61B 5/1036; A61B 5/14552; A61B 5/6829; A61B 5/6892
See application file for complete search history.

(56) References Cited

U.S. PATENT DOCUMENTS

| | | | |
|---|---|---|---|
| 3,970,074 A | 7/1976 | Mogos et al. | |
| 4,374,384 A | 2/1983 | Moates | |

(Continued)

FOREIGN PATENT DOCUMENTS

| | | | |
|---|---|---|---|
| CN | 1308225 A | 8/2001 | |
| CN | 201312800 Y | 9/2009 | |

(Continued)

OTHER PUBLICATIONS

Ammer et al. Thermal Imaging of Skin Changes on the Feet of Type II Diabetics, 2001 Conference Proceedings of the 23rd Annual International Conference of the IEEE Engineering in Medicine and Biology Society, Istanbul, Turkey, Oct. 25-28, 2001, 4 pages.

(Continued)

*Primary Examiner* — Eric F Winakur
*Assistant Examiner* — Abid A Mustansir
(74) *Attorney, Agent, or Firm* — Nutter McClennen & Fish LLP

(57) ABSTRACT

An apparatus for measuring foot blood flow has a platform with a platform contact surface configured to receive a foot force from a user placing their foot on the contact surface. The apparatus also has a plurality of PPG sets (having at least one light source and at least one detector) extending through the platform contact surface, and a plurality of springs. Each PPG set is coupled with one or more of the springs to movably couple with the platform. In addition, each spring is biased to produce a biasing force via its coupled PPG set when the contact surface of the platform (Continued)

receives the foot. To maintain consistent pressure against the skin and good signal to noise ratio, each PPG set and its corresponding one or more springs are configured so that the biasing force has a magnitude that is substantially independent of the foot force magnitude.

38 Claims, 28 Drawing Sheets

(56) References Cited

U.S. PATENT DOCUMENTS

| | | | |
|---|---|---|---|
| 4,574,359 A | 3/1986 | Ishizaka et al. | |
| 4,592,000 A | 5/1986 | Ishizaka et al. | |
| 4,629,336 A | 12/1986 | Ishizaka | |
| 4,647,918 A | 3/1987 | Goforth | |
| 4,648,055 A | 3/1987 | Ishizaka et al. | |
| 4,669,472 A | 6/1987 | Eisenmenger | |
| 4,843,577 A | 6/1989 | Muramoto | |
| 4,849,885 A | 7/1989 | Stillwagon et al. | |
| 4,866,621 A | 9/1989 | Ono | |
| 4,878,184 A | 10/1989 | Okada et al. | |
| 5,011,294 A | 4/1991 | Yamaguchi | |
| 5,015,102 A | 5/1991 | Yamaguchi | |
| 5,066,141 A | 11/1991 | Ikeda et al. | |
| 5,070,932 A | 12/1991 | Vlasak | |
| 5,259,389 A | 11/1993 | Muramoto et al. | |
| 5,352,039 A | 10/1994 | Barral et al. | |
| 5,473,629 A | 12/1995 | Muramoto | |
| 5,546,955 A | 8/1996 | Wilk | |
| 5,642,096 A | 6/1997 | Leyerer et al. | |
| 5,678,566 A | 10/1997 | Dribbon | |
| 5,929,332 A | 7/1999 | Brown | |
| 6,077,228 A | 6/2000 | Schonberger | |
| 6,090,050 A | 7/2000 | Constantinides | |
| 6,195,921 B1 | 3/2001 | Truong | |
| 6,398,740 B1 | 6/2002 | Lavery et al. | |
| 6,631,287 B2 | 10/2003 | Newman et al. | |
| 6,767,330 B2 | 7/2004 | Lavery et al. | |
| 6,807,869 B2 | 10/2004 | Farringdon et al. | |
| 6,963,772 B2 | 11/2005 | Bloom et al. | |
| 7,052,472 B1 | 5/2006 | Miller et al. | |
| 7,167,734 B2 | 1/2007 | Khalil et al. | |
| 7,206,718 B2 | 4/2007 | Cavanagh et al. | |
| 7,318,004 B2 | 1/2008 | Butterfield | |
| 7,563,024 B2 | 7/2009 | Rotem et al. | |
| 7,637,657 B2 | 12/2009 | Yamamoto et al. | |
| 7,716,005 B2 | 5/2010 | Shoureshi et al. | |
| 7,726,206 B2 | 6/2010 | Terrafranca, Jr. et al. | |
| 7,758,523 B2 | 7/2010 | Collings et al. | |
| 8,360,987 B2 | 1/2013 | Kantro et al. | |
| 8,454,539 B2 | 6/2013 | Vuillerme et al. | |
| 9,095,305 B2 | 8/2015 | Engler et al. | |
| 9,259,178 B2 | 2/2016 | Bloom et al. | |
| 9,271,672 B2 | 3/2016 | Linders et al. | |
| 9,326,723 B2 | 5/2016 | Petersen et al. | |
| 11,103,138 B2 | 8/2021 | Linders et al. | |
| 11,304,608 B2 | 4/2022 | Petersen et al. | |
| 11,395,622 B2 | 7/2022 | Linders et al. | |
| 11,627,883 B2 | 4/2023 | Linders et al. | |
| 2002/0082486 A1 | 6/2002 | Lavery et al. | |
| 2002/0143257 A1 | 10/2002 | Newman et al. | |
| 2004/0129463 A1 | 7/2004 | Carlucci et al. | |
| 2005/0165284 A1 | 7/2005 | Gefen | |
| 2006/0021261 A1 | 2/2006 | Face | |
| 2006/0030783 A1 | 2/2006 | Tsai et al. | |
| 2006/0126085 A1 | 6/2006 | Owen et al. | |
| 2007/0038273 A1 | 2/2007 | Bales et al. | |
| 2007/0039211 A1 | 2/2007 | Pichler | |
| 2007/0043408 A1 | 2/2007 | Winnett et al. | |
| 2007/0173727 A1 | 7/2007 | Naghavi et al. | |
| 2008/0109183 A1 | 5/2008 | Shoureshi et al. | |
| 2008/0214962 A1 | 9/2008 | Kantro et al. | |
| 2008/0234943 A1 | 9/2008 | Ray et al. | |
| 2008/0238660 A1 | 10/2008 | Dayton et al. | |
| 2009/0143843 A1 | 6/2009 | Bales et al. | |
| 2009/0219972 A1 | 9/2009 | Carlsson et al. | |
| 2009/0306801 A1 | 12/2009 | Sivak et al. | |
| 2010/0004566 A1 | 1/2010 | Son et al. | |
| 2010/0041998 A1 | 2/2010 | Postel | |
| 2010/0063778 A1 | 3/2010 | Schrock et al. | |
| 2010/0198022 A1 | 8/2010 | Vuillerme et al. | |
| 2010/0268111 A1 | 10/2010 | Drinan et al. | |
| 2010/0324455 A1 | 12/2010 | Rangel et al. | |
| 2011/0015498 A1 | 1/2011 | Mestrovic et al. | |
| 2011/0054359 A1 | 3/2011 | Sazonov et al. | |
| 2011/0122251 A1 | 5/2011 | Schmidt | |
| 2011/0214501 A1 | 9/2011 | Ross et al. | |
| 2011/0215930 A1 | 9/2011 | Lee et al. | |
| 2011/0263950 A1 | 10/2011 | Larson et al. | |
| 2011/0275956 A1 | 11/2011 | Son et al. | |
| 2011/0313314 A1 | 12/2011 | Gefen | |
| 2012/0020573 A1 | 1/2012 | Kacenjar | |
| 2012/0035509 A1 | 2/2012 | Wilson et al. | |
| 2012/0086550 A1 | 4/2012 | LeBlanc et al. | |
| 2012/0109013 A1 | 5/2012 | Everett et al. | |
| 2012/0190989 A1 | 7/2012 | Kaiser et al. | |
| 2012/0221286 A1 | 8/2012 | Bisch et al. | |
| 2013/0019503 A1 | 1/2013 | Vogt | |
| 2013/0162796 A1 | 6/2013 | Bharara et al. | |
| 2013/0211281 A1 | 8/2013 | Ross et al. | |
| 2013/0261494 A1 | 10/2013 | Bloom et al. | |
| 2013/0261495 A1 | 10/2013 | Linders et al. | |
| 2013/0261496 A1 | 10/2013 | Engler et al. | |
| 2015/0057562 A1 | 2/2015 | Linders et al. | |
| 2015/0190059 A1 | 7/2015 | Petersen et al. | |
| 2015/0206301 A1 | 7/2015 | Mestha et al. | |
| 2015/0359457 A1 | 12/2015 | Blumenthal et al. | |
| 2016/0100790 A1 | 4/2016 | Cantu et al. | |
| 2016/0192844 A1 | 7/2016 | Linders et al. | |
| 2016/0256056 A1 | 9/2016 | Petersen et al. | |
| 2017/0127999 A1 | 5/2017 | Linders et al. | |
| 2017/0188841 A1 | 7/2017 | Ma et al. | |
| 2017/0188964 A1 | 7/2017 | Banet et al. | |
| 2018/0014734 A1 | 1/2018 | Rogers et al. | |
| 2018/0132730 A1 | 5/2018 | Linders et al. | |
| 2018/0144815 A1 | 5/2018 | Chapman-McQuiston et al. | |
| 2018/0249945 A1 | 9/2018 | Najafi et al. | |
| 2020/0113510 A1 | 4/2020 | Linders et al. | |
| 2021/0212628 A1 | 7/2021 | Peterson et al. | |
| 2021/0386297 A1 | 12/2021 | Linders et al. | |
| 2022/0211277 A1 | 7/2022 | Petersen et al. | |

FOREIGN PATENT DOCUMENTS

| | | |
|---|---|---|
| CN | 202263087 U | 6/2012 |
| DE | 202010013176 U1 | 2/2011 |
| DE | 202014105408 U1 | 11/2014 |
| EP | 0885587 A1 | 12/1998 |
| EP | 1511419 B1 | 8/2008 |
| JP | 55071919 A | 5/1980 |
| JP | H03-275039 A | 12/1991 |
| JP | 2002-269231 A | 9/2002 |
| JP | 2004-528085 A | 9/2004 |
| JP | 2005-533543 A | 11/2005 |
| JP | 2009-539454 A | 11/2009 |
| JP | 2011508243 A | 3/2011 |
| JP | 2013/151705 A | 8/2013 |
| KR | 101027367 B1 | 4/2011 |
| KR | 10-2012-0007154 A | 1/2012 |
| NZ | 514340 A | 1/2004 |
| RU | 2433783 C2 | 11/2011 |
| WO | 01/89367 A2 | 11/2001 |
| WO | 2007/114768 A1 | 10/2007 |
| WO | 2008/058051 A2 | 5/2008 |
| WO | 2009/005373 A1 | 1/2009 |
| WO | 2010/021932 A2 | 2/2010 |
| WO | 2010/085163 A1 | 7/2010 |
| WO | 2012/051394 A1 | 4/2012 |
| WO | 2012055029 A1 | 5/2012 |
| WO | 2012/084814 A1 | 6/2012 |
| WO | 2013/114291 A1 | 8/2013 |
| WO | 2013/151705 | 10/2013 |

(56) References Cited

FOREIGN PATENT DOCUMENTS

| WO | 2015143218 A1 | 9/2015 |
|---|---|---|
| WO | 2018175787 A1 | 9/2018 |
| WO | 2021022363 A1 | 2/2021 |

OTHER PUBLICATIONS

Armstrong et al. Monitoring Healing of Acute Charcot's Arthropathy with Infrared Dermal Thermometry, Journal of Rehabilitation Research and Development, vol. 34, No. 3, Jul. 1997, pp. 317-321.
Bagavathiappan, S., et al., "Correlation between Plantar Foot Temperature and Diabetic Neuropathy: A Case Study by Using an Infrared Thermal Imaging Technique," Journal of Diabetes Science and Technology, vol. 4, Issue 6, Nov. 2010, 7 pages.
Balbinot, L., et al., "Plantar Thermography is Useful in the Early Diagnosis of Diabetic Neuropathy," 2012 Clinics, pp. 1419-1425, 7 pages.
Balbinot, L., et al., "Repeatability of Infrared Plantar Thermography in Diabetes Patients: A Pilot Study," Journal of Diabetes Science Technology, vol. 7, Issue 5, Sep. 2013, pp. 1130-1137, 9 pages.
Bharara et al. "Coming events cast their shadows before: detecting inflammation in the acute diabetic foot and the foot in remission," Diabetes/Metabolism Research and Reviews, 2012, vol. 28, pp. 15-20.
Bharara, M. Bharara, M-P—Technology Summary, 5 pages, undated.
Bloom, Declaration of Jonathan D. Bloom under 37 CFR § 1.56, pp. 1-3, Feb. 28, 2016.
Brioschi et al. "Automated Computer Diagnosis of IR Medical Imaging," FLIR Technical Series, Application Note for Research & Science, FLIR Systems, Inc., 2011.
Canadian Patent Office, Office Action for Canadian Patent Application No. 3,113,079 dated Feb. 14, 2023 (4 pages).
Caselli, M.D. et al. "The Forefoot-to-Rearfoot Plantar Pressure Ratio is Increased in Severe Diabetic Neurpathy and Can Predict Foot Ulceration," Diabetes Care, vol. 25, No. 6, Jun. 2002, pp. 1066-1071.
Cavalheiro, A., et al., Thermographic Analysis and Autonomic Response in the Hands of Patients with Leprosy, An Bras Dermatol, 2016, 274-283, 10 pages.
Chen et al. "Development of a Thermal and Hyperspectral Imaging System for Wound Characterization and Metabolic Correlation," John Hopkins Apl Technical Digest, vol. 26, No. 1, 2005, pp. 67-74.
Chien et al. "Selection and ordering of feature observations in a pattern recognition system." Info and Control 12, No. 5. 1968, pp. 394-414.
Chinese National Intellectual Property Administration, Office Action, Application No. 201580015377.7, dated Aug. 16, 2019, 9 pages.
Chinese National Intellectual Property Administration, Office Action, Application No. 201580015377.7, dated Jan. 8, 2019, 9 pages.
Dabiri et al. "Electronic Orthotics Shoe: Preventing Ulceration in Diabetic Patients," 30th Annual International IEEE EMBS Conference, Aug. 2008, pp. 771-774.
Engler. "Rock Health Presentation" of Aug. 24, 2012, 19 pages.
Engler. Declaration of Jeffrey M. Engler under 37 CFR § 1.56, Feb. 28, 2016, 2 pages.
Evans, A.L., et al., "Thermography in Lower Limb Arterial Disease," Clin. Radiol. (1976) vol. 27, 6 pages.
Frykberg et al. Feasibility and Efficacy of a Smart Mat Technology to Predict Development of Diabetic Plantar Ulcers, Diabetes Care, vol. 40, Jul. 2017, pp. 973-980.
Gatt, A., et al., "Establishing Differences in Thermographic Patterns between the Various Complications in Diabetic Foot Disease," Hindawi International Journal of Endocrinology, vol. 2018, Article ID 98208295, Mar. 12, 2018, 8 pages.
Gatt, A., et al., "The Application of Medical Thermography to Discriminate Neuroischemic Toe Ulceration in the Diabetic Foot," The International Journal of Lower Extremity Wounds, 2018, 4 pages.
Gatt, A., et al., "The Identification of Higher Forefoot Temperatures Associated with Peripheral Arterial Disease in Type 2 Diabetes Mellitus as Detected by Thermography," Primary Care Diabetes, 2018, 7 pages.
Hauer, J., "Hand Skin Blood Flow in Diabetic Patients With Automatic Neuropathy and Microangiopathy," Diabetes Care, vol. 14, No. 10, Oct. 1991, 6 pages.
Ilo, A., et al., "Infrared Thermography and Vascular Disorders in Diabetic Feet," Journal of Diabetes Science and Technology, 2019, 9 pages.
Ilo, A., et al., "Infrared Thermography and Vascular Disorders in Diabetic Feet," Journal of Diabetes Science and Technology, 2020, vol. 14, 9 pages.
International Preliminary Report on Patentability for International Application No. PCT/US2013/030997, dated Jul. 8, 2013, 13 pages.
International Preliminary Report on Patentabilty for International Application No. PCT/US2014/052672 dated Mar. 10, 2016, 6 pages.
International Preliminary Report on Patentabilty for International Application No. PCT/US2017/059674 dated May 23, 2019, 10 pages.
International Preliminary Report on Patentabilty for International Application No. PCT/US2019/056325 dated Apr. 14, 2021, 13 pages.
International Search Report and Written Opinion for International Application No. PCT/US2021/012698 dated Apr. 2, 2021, 19 pages.
International Search Report and Written Opinion for International Application No. PCT/US2016/060638 dated Mar. 2, 2017, 11 pages.
International Search Report and Written Opinion for International Application No. PCT/US2019/056325, dated Dec. 23, 2019.
International Search Report and Written Opinion for International Application No. PCT/US22/51999, dated Mar. 20, 2023 (9 pages).
Isaac et al. "Angiosomal Interpretation of Dermal Thermometry in Patients at High Risk for Diabetic Foot Ulcers." in 2018 Diabetic Limb Salvage Conference, 1 page.
Japanese Patent Office, Decision of Refusal, Application No. 2016-558325, dated Sep. 2, 2019, 10 pages, together with English translation.
Kaabouch et al. "Predicting neurpathic ulceration: analysis of static temperature distributions in thermal images," Journal of biomedical Optics, vol. 15, Sec. 6, 2010, p. 061715-1-061715-6.
Lavery et al. Unilateral remote temperature monitoring to predict future ulceration for the diabetic foot in remission. BMJ Open Diabetes Research and Care, 7(1), 2019, 7 pages.
Lin, P, et al., "Assessment of Lower Extremity Ischemia Using Smartphone Thermographic Imaging", Journal of Vascular Surgery Cases and Innovative Techniques, Dec. 2017, 4 pages.
Liu et al. "Infrared Dermal Thermography on Diabetic Feet Soles to Predict Ulcerations: a Case Study," Proc. of SPIE, vol. 8572, 2013, pp. 85720N01-85720N-9.
Liu et al. "Statistical analysis of spectrial data: a methodology for designing an intelligent monitoring system for the diabetic foot," Predicting neuropathic ulceration: analysis of static temperature distributions in thermal images, Journal of Biomedical Opitcs, vol. 18(12), Dec. 2013, pp. 126004-1-126004-11.
Liu et al., "Automatic detection of diabetic foot complications with infrared thermography by asymmetric analysis," Journal of Biomedical Optics, 20(2), 2015 (11 pages).
McLoughlin, G., et al., "Thermography in the Diagnosis of Occlusive Vascular Disease of the Lower Limb," Brit. J. Surg., Aug. 1973, vol. 60, No. 8, 2 pages.
Medcitynews.com, Description of Public Disclosures reported in Medcitynews.com and CloudTop Articles along with Exhibits A-D, 32 pages, Sep. 2015.
Medgadget.com "TempTouch for Foot Ulcer Detection," Xilas, Inc., Apr. 19, 2005, 2 pages.
Morley et al. "In Shoe-Multisensory Data Acquisition System," IEEE Transactions on Biomedical Engineering, vol. 48, No. 7, Jul. 2001, pp. 815-820.
Najafi B, et al., Plantar Temperature Response to Walking in Diabetes with and without Acute Charcot: The Charcot Activity Response Test, J of Aging Res, Jun. 25, 2012, Hindawi Pub Corp, vol. 2012, doi:10.1155/2012/140968 (Year: 2012).

(56) References Cited

OTHER PUBLICATIONS

Notice of Opposition to a European Patent—European Patent No. 2833783B1, dated May 31, 2018, 8 pages.
Park, E., et al., "Comparison of Sympathetic Skin Response and Digital Infrared Thermographic Imaging in Peripheral Neuropathy," Yonsei Medical Journal, vol. 35, No. 4, 1994, 9 pages.
Peleki, A., et al., "Novel Use of Smartphone-based Infrared Imaging in the Detection of Acute Limb Ischaemia," EJVES Short Reports (2016) 32, 3 pages.
Roback "An overview of temperature monitoring devices for early detection of diabetic foot disorders," Linkoping University Post Print, 2010, 18 pages.
Sagaidachnyi, A., et al., "Thermography-based Blood Flow Imaging in Human Skin of the Hands and Feet: A Spectrum Filtering Approach," Institute of Physics and Engineering in Medicine, Physiol. Meas. 38 (2017), 18 pages.
Schmidt, B., et al., "Describing Normative Foot Temperatures in Patients With Diabetes-Related Peripheral Neuropathy," Journal of Diabetes Science and Technology 2020, vol. 14, 6 pages.
Sebastian, A. et al., "Clinical Features, Radiological Characteristics and Offloading Modalities in Stage0 Acute Charcot's Neuroarthropathy—A Single Centre Experience from South India," Diabetes & Metabolic Syndrome: Clinical Research & Review, 13 (2019), 5 pages.
Siren Care "Siren Care—Best Diabetic Socks Tracking Your Foot Health," http://siren.care/how-it-works, Jan. 6, 2017, 4 pages.
Staffa, E., "Infrared Thermography as Option for Evaluating the Treatment Effect of Percutaneous Transluminal Angioplasty by Patients with Peripheral Arterial Disease," Vascular Online, first published on Mar. 17, 2016, 8 pages.
Supplementary European Search Report for Application No. EP 13772800, dated Jun. 26, 2015, 7 pages.
Supplementary European Search Report for Application No. PCT/US2019056325, No. 19874565.5, dated Jun. 9, 2022 (7 pages).
Supplementary European Search Report for European Patent Application No. 16863080, dated Apr. 30, 2019 (12 pages).
Theuma, F., et al., The Use of Smartphone-attached Thermography Camera in Diagnosis of Acute Lower Limb Ischemia, Society for Vascular Surgery, Submitted Feb. 19, 2017; Accepted Feb. 23, 2017, 1 page.
Van Netten et al. "Infrared Thermal Imaging for Automated Detection of Daibetic Foot Complications" Journal of Diabetes Science and Technology, vol. 7, Issue 5, Sep. 2013, pp. 1122-1129.
Visual Footcare Technologies, LLC. "TempStat," Visual Footcare Technologies, LLC, Thermal Imaging Device, One unit: $125, undated, 1 page.
Wallace, G., et al., "The Use of Smart Phone Thermal Imaging for Assessment of Peripheral Perfusion in Vascular Patients" Annals of Vascular Surgery (accepted manuscript) 2017, 18 pages.

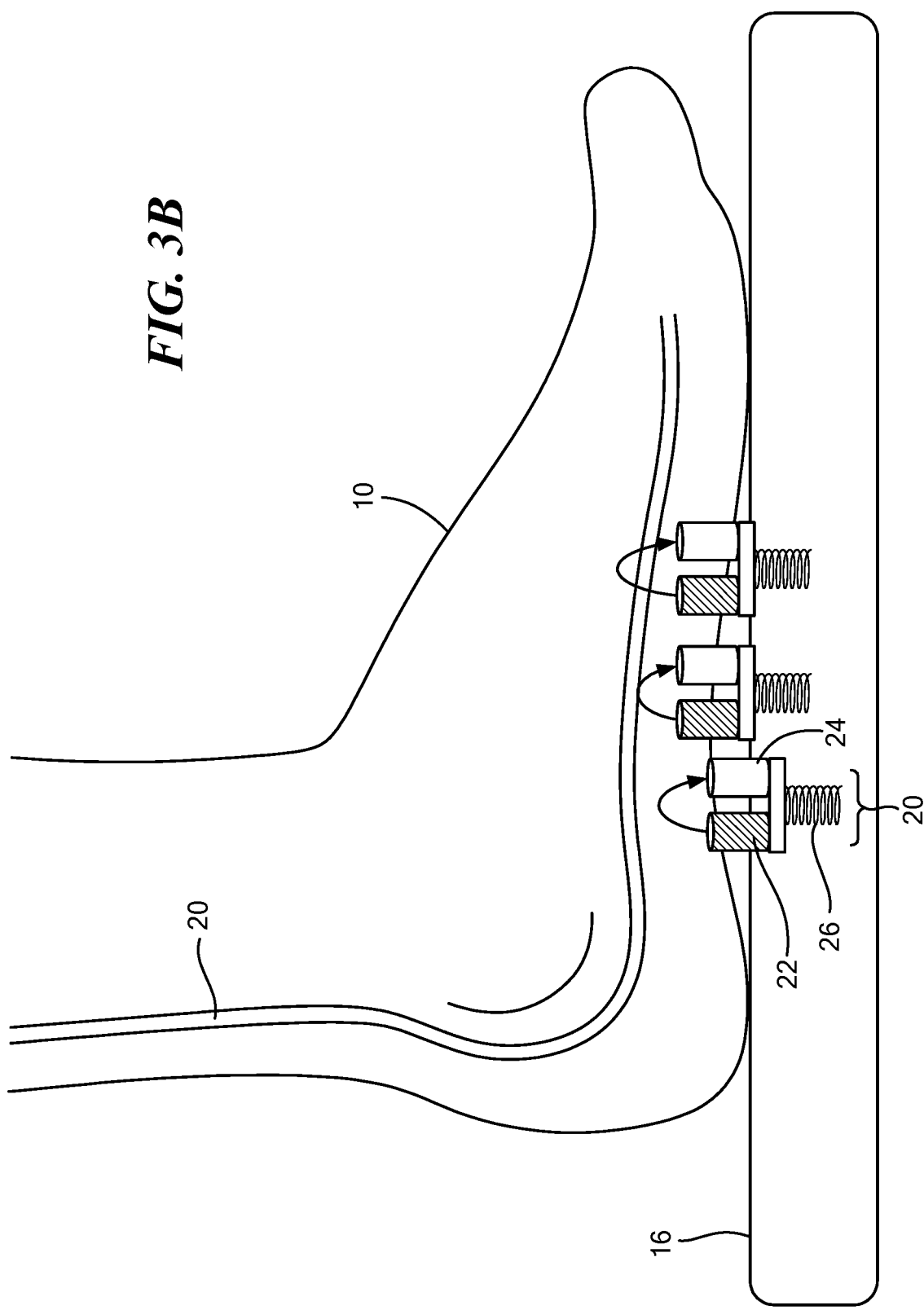

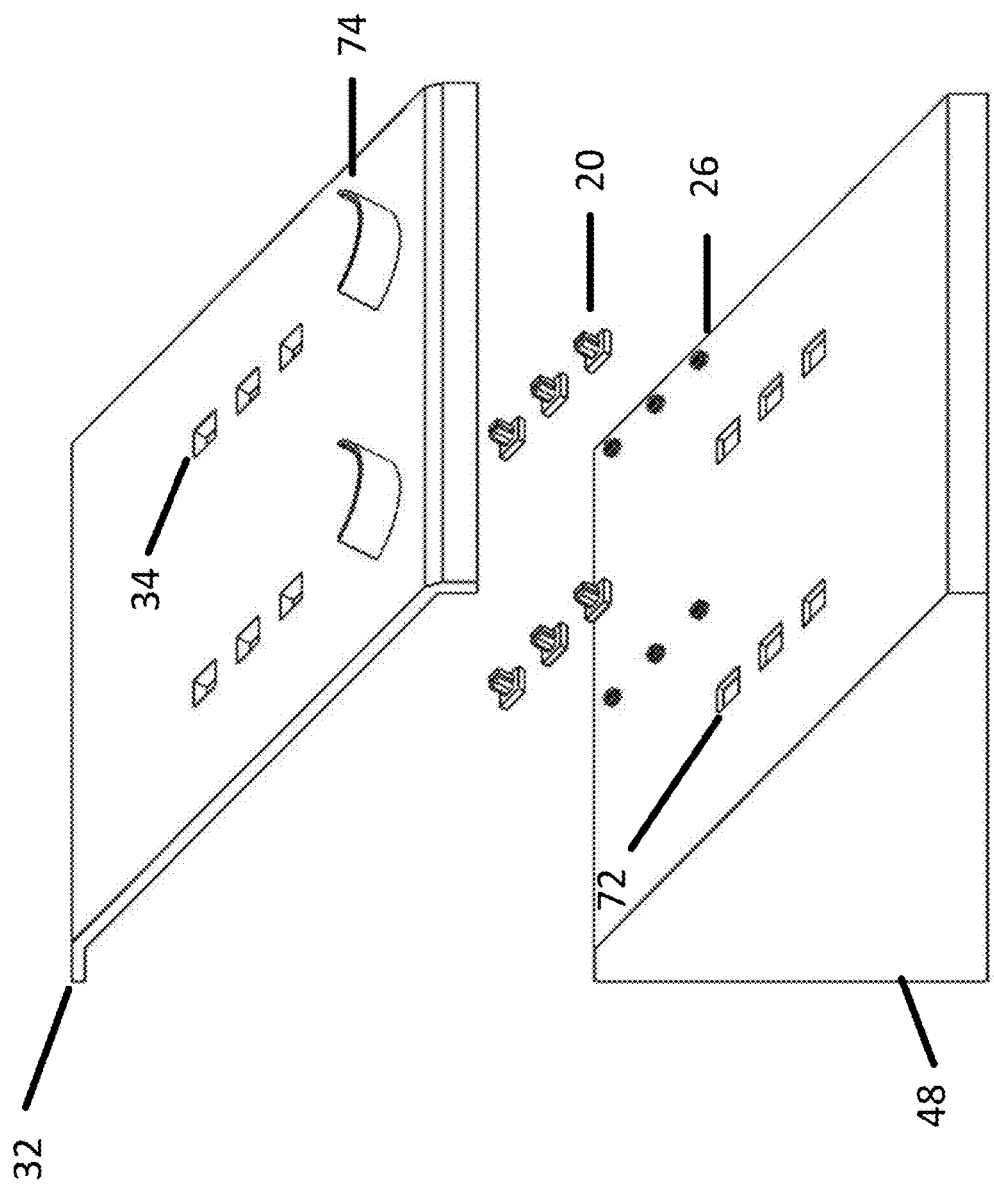

APPARATUS AND METHOD OF MEASURING BLOOD FLOW IN THE FOOT

PRIORITY

This patent application claims priority from provisional U.S. patent application No. 63/286,352, filed Dec. 6, 2021, entitled, "BLOOD FLOW MEASUREMENTS USING PHOTOPLETHYSMOGRAPHY, the disclosure of which is incorporated herein, in its entirety, by reference.

FIELD

Illustrative embodiments of the invention generally relate to measuring blood flow and, more particularly, various embodiments of the invention relate to measuring blood flow in the foot.

BACKGROUND

Many Americans living with diabetes also develop cardiovascular diseases and other cardiac comorbidities. Many of these comorbidities, such as ulceration or peripheral arterial disease, can present its complications in the foot, making it a vulnerable area on the body for diabetic patients. Changes in blood flow to the foot could be indicative of early signs of such complications.

SUMMARY OF VARIOUS EMBODIMENTS

In accordance with one embodiment of the invention, an apparatus for measuring foot blood flow has a platform with a platform contact surface configured to receive the foot. The platform contact surface is configured to receive a foot force having a foot force magnitude when the platform contact surface receives the foot (e.g., when the foot is at rest on the platform contact surface). The apparatus also has a plurality of PPG sets (having at least one light source and at least one detector) extending through the platform contact surface, and a plurality of springs. Each PPG set is coupled with one or more of the springs to movably couple with the platform. In addition, each spring is biased to produce a biasing force via its coupled PPG set when the contact surface of the platform receives the foot. To maintain consistency, each PPG set and its corresponding one or more springs are configured so that the biasing force has a biasing force magnitude that is substantially independent of the foot force magnitude.

Specifically, the plurality of PPG sets may have a first PPG set with a first spring having a first spring constant, and a second PPG set with a second spring having a second spring constant. To vary the biasing force, the first spring constant may be different from the second spring constant. In addition or alternatively, the first PPG set may have a first top contact surface spaced a first distance from the contact surface of the platform, while the second PPG set has a second top contact surface spaced from a second distance from the platform contact surface. Because the foot may not be flat, the first distance may be greater than the second distance. In other embodiments, the first and second distances may be the same.

To improve readings, the plurality of PPG sets may be configured to produce a plurality of different wavelengths of light at the same time. Moreover, the platform contact surface may form a plurality of apertures that each contain at least one of the PPG sets and corresponding spring(s). Each PPG set preferably is constrained to move in one dimension/direction; typically configured to move normal to the surface within the aperture in response receipt of the foot force. Some embodiments, however, may move each PPG set in a direction not-normal to the surface In addition, as noted above, the plurality of PPG sets has a top contact surface configured to contact the foot. The springs may be configured to permit the top contact surface to be movable to be substantially flush or below the level of the platform contact surface in response to the foot force.

Those skilled in the art may select from any of a variety of types of springs. For example, the plurality of springs may include one or more of a coil spring, a leaf spring, a cantilever spring, a foam spring, a viscoelastic ("memory") foam/spring and/or an elastomeric spring. In a similar manner, those skilled in the art may select any of a variety of types of light sources. For example, at the light source may include a light emitting diode or laser. The at light detector may include a photodetector.

Preferably, the spring biasing force is strong enough to minimize light leakage at the interface of the light source and skin of the foot. To that end, the spring for a given PPG set may be configured to cause no reflective light to leak from the light source when abutting the foot. For example, the biasing force may range from 1 N to 10 N The platform can be configured in any of a variety of modalities. For example, the platform may be in the form of an open platform (e.g., resembling a bathroom scale, floor mat, or rug) or a closed platform (e.g., a shoe, insole, or sock). Regardless of the modality, the platform may have guide indicia identifying where to place a foot on the platform. The platform may also have a visual display configured to show measurement status.

Other sensors may provide further functionality. For example, the platform may have a placement system configured to start analyzing a foot in response to measurements of at least one PPG set and/or a pressure sensor. Moreover, in some embodiments, the plurality of PPG sets are arranged as a two-dimensional array of PPG sets extending from the platform contact surface. This array may be in the form of a single array, or as a plurality of arrays (e.g., one array for the left foot and another array for the right foot).

In accordance with another embodiment, an apparatus for measuring blood flow in a foot has a platform with a platform contact surface configured to receive the foot. The platform contact surface is configured to receive a foot force having a foot force magnitude when the platform contact surface receives the foot. The platform also has a pair of PPG sets. Specifically, the platform has 1) a first PPG set with a first light detector and a first light source configured to emit light at a first wavelength, and 2) a second PPG set with a second light detector and a second light source configured to emit light at a second wavelength. The first and second PPG sets normally extend above the platform contact surface. The first wavelength and the second wavelength preferably are different. Preferably, the first PPG set is configured to emit light at the first wavelength at the same time that the second PPG set emits light at the second wavelength.

The platform also has a first spring, coupled with the first PPG set, to movably couple the first PPG set with the platform. The first spring is biased to produce a first biasing force via the first PPG set when the contact surface of the platform receives the foot. In a similar manner, the platform has a second spring, coupled with the second PPG set, to movably couple the second PPG set with the platform. The second spring is biased to produce a second biasing force via the second PPG set when the contact surface of the platform receives the foot. The platform contact surface forms a first aperture at least in part containing the first PPG set and the first spring, and a second aperture at least in part containing the second PPG set and the second spring. Correspondingly, the first PPG set is configured to move within the first aperture, while the second PPG set is configured to move within the second aperture. Preferably, the first PPG set and the first spring configured are so that the first biasing force has a magnitude substantially independent of the foot force magnitude.

In accordance with other embodiments, a method of measuring blood flow in a foot positions a foot on a platform having a plurality of PPG sets and a platform contact surface with a plurality of aperture. Each PPG set has at least one light source and at least one light detector and is biased toward the foot through one of the apertures in the platform contact surface. The foot produces a foot force toward the contact surface when positioned on the platform contact surface. The method then produces, by each PPG set, a biasing force with a magnitude substantially independent of the foot force, directs, by the PPG sets, light into the foot, and receives, by the PPG sets, reflection of the light directed into the foot. The method then determines a blood flow characteristic (e.g., heart rate, blood oxygenation, regional differences in tissue oxygenation, and/or blood perfusion, among others) from the received light.

Illustrative embodiments of the invention are implemented as a computer program product having a computer usable medium with computer readable program code thereon. The computer readable code may be read and utilized by a computer system in accordance with conventional processes.

BRIEF DESCRIPTION OF THE DRAWINGS

Those skilled in the art should more fully appreciate advantages of various embodiments of the invention from the following "Description of Illustrative Embodiments," discussed with reference to the drawings summarized immediately below.

DESCRIPTION OF ILLUSTRATIVE EMBODIMENTS

Figure 1:
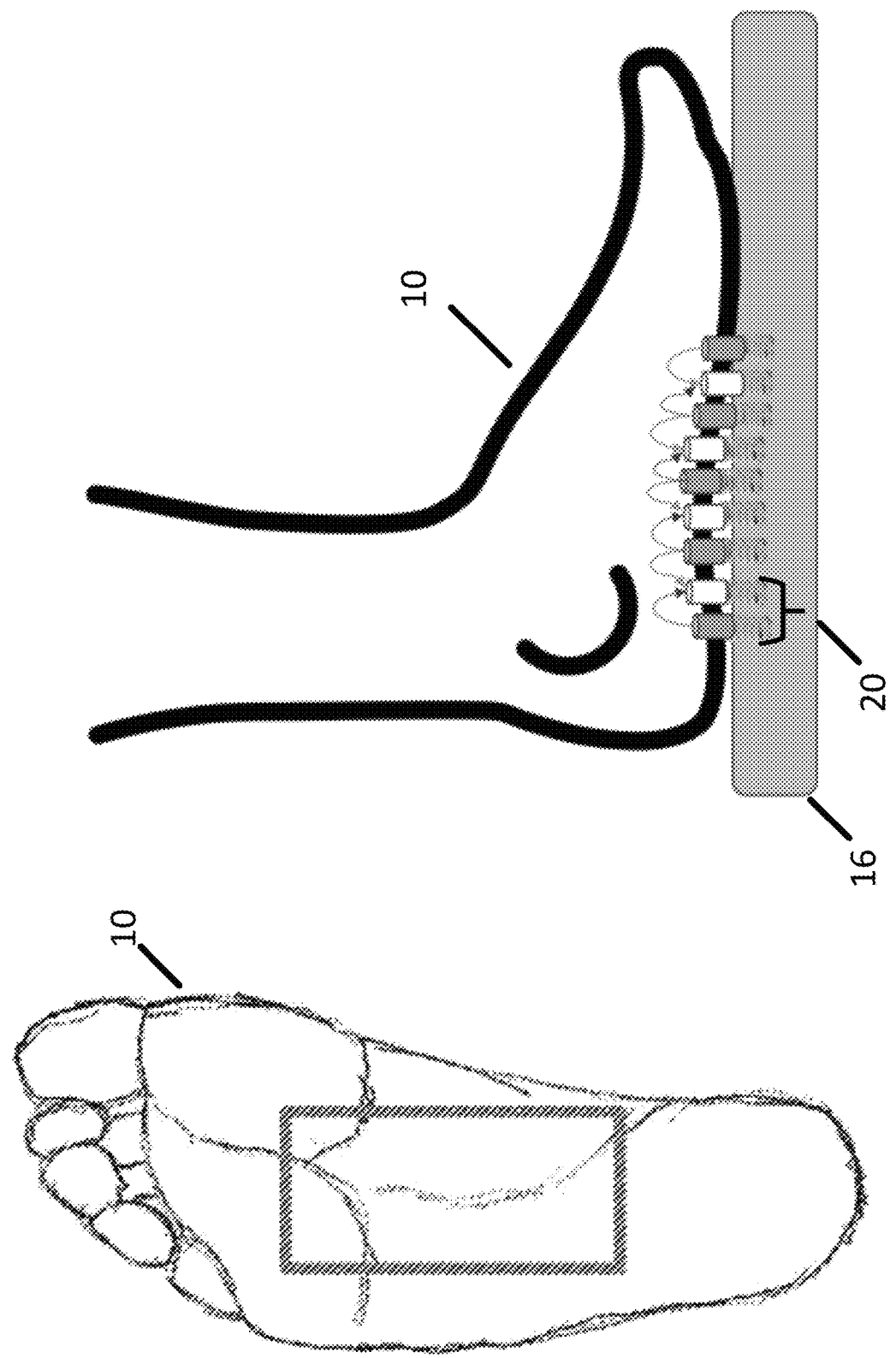
FIGS. 1A and 1B schematically show an illustration of the plantar region (e.g. sole) of a foot, FIG. 1B schematically illustrates a user's foot positioned on a platform, FIG. 2 schematically shows an illustration of a PPG set mounted in platform, FIG. 3A schematically shows a cross section of a foot while PPG measurements are being performed, FIG. 3B schematically illustrates a cross section of a foot while PPG measurements are being performed, FIG. 3C schematically illustrates one embodiment of an open platform to perform PPG measurements, FIG. 3D schematically illustrates one embodiment of a closed platform to perform PPG measurements, FIG. 4A schematically show one form factor of an open platform that gathers data about that user's feet, FIG. 4B schematically show one form factor of an open platform that gathers data about that user's feet, FIG. 5A schematically shows an isometric view of one embodiment of open platform, FIG. 5B schematically shows an exploded view of one embodiment of open platform, FIG. 5C schematically shows a cross sectional view one embodiment of an open platform, FIG. 6A schematically shows an isometric view of one embodiment of open platform, FIG. 6B schematically shows an exploded view of one embodiment of open platform, FIG. 6C schematically shows a cross sectional view one embodiment of an open platform, FIG. 7A schematically shows an isometric view of one embodiment of open platform, FIG. 7B schematically shows an exploded view of one embodiment of open platform, FIG. 7C schematically shows a cross sectional view one embodiment of an open platform, FIG. 8 schematically shows one embodiment in which a platform can communicate with a larger data network, FIG. 9 schematically shows one embodiment of a block diagram of a foot monitoring system, FIG. 10 schematically shows a block diagram of one embodiment of the various components in the platform.

In illustrative embodiments, a method and apparatus analyze a patient's foot to determine the blood flow of a patient's foot through photoplethysmography ("PPG") measurements. Among other ways, those measurements may be taken from the plantar surfaces of the feet of patients (e.g., the sole of the foot). A plurality of light sources, such as lasers and/or light emitting diodes (LEDs), are coupled with a photodetectors to form PPG sets positioned against the sole of the patient's/user's foot. The light source in each PPG sets transmits light of a given wavelength into the surface of the foot and the detector measures an intensity of the light signal that can be detected through the sole of the foot. The change of the intensity of the light absorbed represents blood volume changes in the microvascular bed of the plantar tissue. The measured PPG signal is analyzed to determine cardiac health parameters, which may include heart rate, heart rate variability (HRV), respiration rate, and oxygen saturation ($SpO_2$), blood perfusion in the feet, and regional differences in the blood flow and tissue oxygenation between the feet and in different portions of the feet.

The PPG sets are coupled with springs that are movably coupled with to a platform (e.g., a rigid platform or flexible platform). A user contacts the rigid platform with the bottom of one or both of the user's feet and the springs are biased to hold the PPG sets against the sole (e.g., plantar region) of the user's foot. In some embodiments, the user may stand on the rigid platform, or may place their feet on the rigid platform while sitting or reclining. The biasing force of the spring coupled to the PPG pair is substantially independent of the force of the user's foot against the rigid platform. Accordingly, the biasing force applied to the patient's foot is the same regardless of the patient's position, intended interaction with the PPG pair, or weight.

The specific wavelengths of the light sources may range from the visible light wavelengths to infra-red (IR) wavelengths. In particular, the PPG light source may use red, infrared, and/or green lasers and/or LEDs.

The platform takes PPG measurements from some or all of the PPG sets and records those readings in memory. A feedback mechanism may be included for users to visually observe part of or the entire process, such as when: a) the PPG reading begins; b) it is in progress; and c) the process is successfully completed. The feedback may be in the form of visual, acoustic, or other indicia, such as lights, sounds, or a graphical user interface (GUI) with visual indicia (e.g., words or numbers).

A data file containing the recorded data may be transmitted to a remote processor. In illustrative embodiments, a platform uses this data with signal processing and filtering functionality, as well as with a process to calculate heart rate and/or signal-to-noise ratio. This permits patients, their health care providers, and/or their caregivers to intervene earlier, reducing the risk of more serious complications. Details of illustrative embodiments are discussed below.

As known by those in the art, photoplethysmography (PPG) is a simple and low-cost optical technique that can be used to detect blood volume changes in the microvascular bed of tissue. It is often used non-invasively to make measurements at the skin surface. The PPG waveform comprises a pulsatile ("AC") physiological waveform attributed to cardiac synchronous changes in the blood volume with each heartbeat, and is superimposed on a slowly varying ("DC") baseline with various lower frequency components attributed to respiration, sympathetic nervous system activity and thermoregulation.

Although the origins of the components of the PPG signal are not fully understood, it is generally accepted that they can provide valuable information about the cardiovascular system. PPG products can be implemented using low cost, simple and portable technology for the primary care and community based clinical settings. This is facilitated by the wide availability of low cost and small semiconductor components, and the advancement of computer-based pulse wave analysis techniques. The PPG technology has been used in a wide range of commercially available medical devices for measuring oxygen saturation, blood pressure and cardiac output, assessing autonomic function and also detecting peripheral vascular disease.

Foot photoplethysmograms therefore include physiological information from the heart towards the lower extremities because PPG detects light variations originating from changes in the blood volume being transmitted from the left ventricle. Previous studies have reported various medical applications of foot PPG, including the monitoring of the vascular status, the prevention of diabetic foot ulcers FIG. 1A schematically shows the plantar region (e.g., sole) of a foot 10 with a box indicating a region of the fore foot that is particularly useful when making PPG measurements. On and around the forefoot, one or more PPG sets can target three or more key locations for each foot: the lateral plantar artery, medial plantar artery, and deep plantar artery. In one embodiment, PPG sets are positioned at the midfoot of each foot (about halfway of a universal foot), and the sensors are positioned with a pitch of 35-45 mm (e.g., 39 mm) from each other.

Alternative embodiments use other locations on the foot to collect PPG signals (e.g., for redundancy and accuracy despite foot morphology differences or motion during scanning) and to measure relative blood flow differences across the foot. PPG signals may be collected from regions of the sole of the foot that has thicker skin, such as the heel and the ball, as well as regions that have thinner skin, such as the midfoot.

FIG. 1B schematically illustrates a user's foot 10 positioned on a rigid platform 16. PPG sets 20 are shown coupled to the rigid platform 16 with springs, and the PPG sets 20 are being held in contact with the plantar surface of the user's foot by the pressure applied toward the foot by the springs. The light source illuminates the skin and the detector measures changes in light absorption. In this way, the PPG set monitors the perfusion of blood to the dermis and subcutaneous tissue of the skin. This is schematically represented by the curved arrows in FIG. 1B illustrating a light signal that emanates from the source and is measured at the detector. Accordingly, in illustrative embodiments, light from the light source penetrates into the foot and reflects back to the detector.

Figure 2:
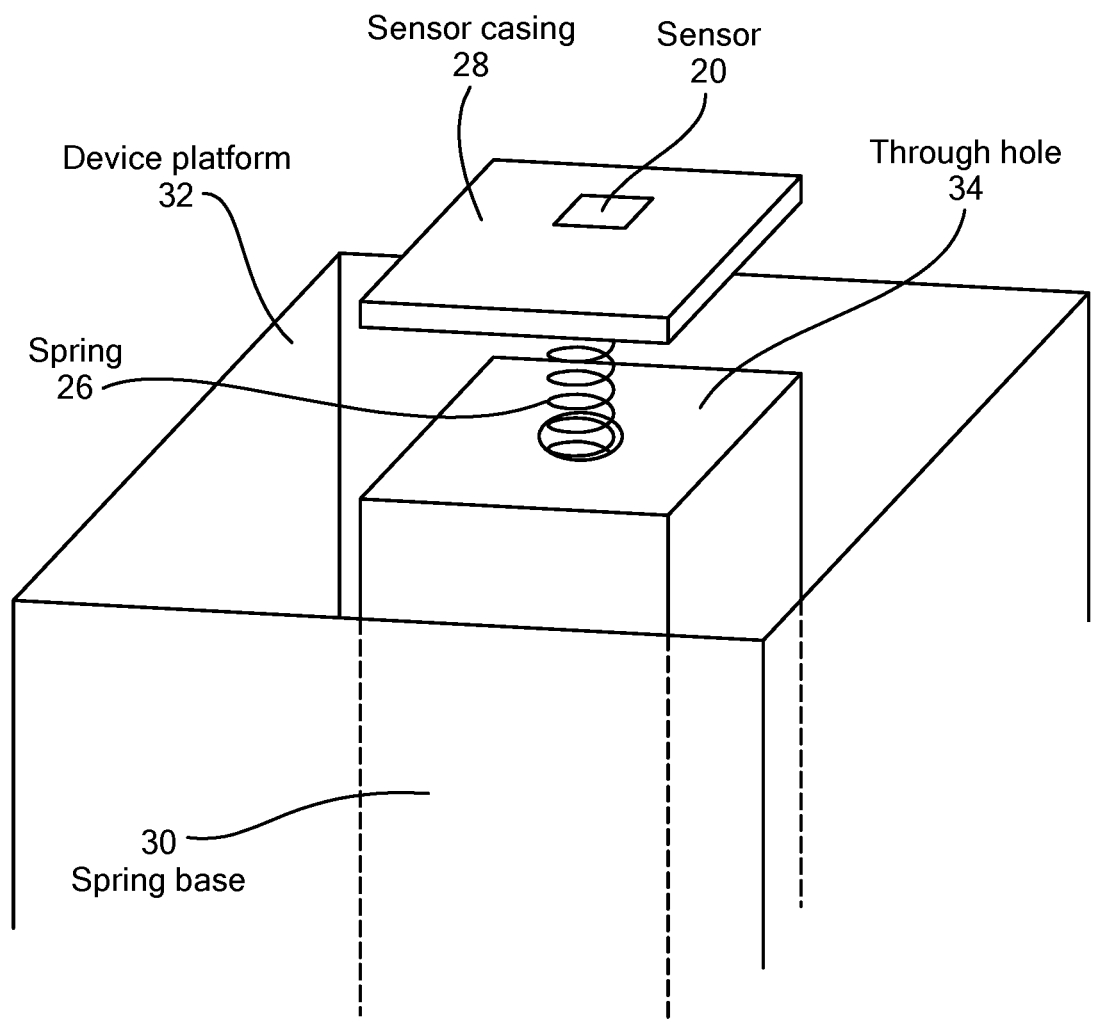

A simplified schematic illustration of a sensor 20 (e.g., PPG set) mounted in a rigid platform is shown in FIG. 2. In this embodiment, the light source and the detector (e.g., PPG set) are shown as a sensor 20 being mounted in a PPG set casing/housing 28 (e.g., sensor casing) that is coupled to a spring 26 mounted on a spring base 30. The PPG sensor 20 may move freely up and down on the spring 26 within a through hole 34 in a cover 32 of a device platform 16 (e.g., rigid platform). It is this device platform 16, or its top surface, that supports the weight or force of the foot (e.g., the full weight if the patient is standing, or the reduced force if the foot is simply placed against it). As noted above and below, the spring 26 produces a return/biasing force that is substantially independent of the force on the platform.

The spring keeps the PPG set casing 20 firmly against the sole of the foot. Preferably, the PPG set 20 and spring 26 effectively move like a plunger in that they are constrained to move in one direction (e.g., generally normal to the surface of the rigid platform 16). In some embodiments, the detector and the light source may be mounted on separate springs so that they may each move independently. The detector and light source may be mounted on springs with the same force constant or different force constants.

The encased sensors 20 can be directly or indirectly connected to a spring 26 affixed to the base of the device. The encased sensor 20 may be movably coupled within the through hole 34 in a manner that enables the sensor 20 to move up and down through the hole 34 as pressure is applied. This movement may be substantially normal to the top surface of the platform or at a non-normal angle to the top surface. Depending on the location of the foot, the spring heights and strengths can be altered to achieve the best signal possible. For example, one or more springs may be nominally set so that when at rest (i.e., when the foot is not on the platform), their corresponding PPG sets are about 7.4 mm above the top surface of the platform to target the deep plantar artery, about 15.4 mm above the top surface of the platform to target the medial plantar artery, and about 11.4 mm above the top surface of the platform to target the lateral plantar artery.

The springs preferably are configured to apply a moderated force to the foot so as not to unduly constrict blood flow. At the same time, the spring force (aka "biasing force") should be significant enough to both minimize light scattering at the interface of the light source and maximize light capture at the detector. To those ends, springs on PPG sets targeting the deep plantar artery and lateral plantar artery can be configured to a variety of dimensions, stiffnesses, for example, with a spring constant of 1.0 N/mm. Furthermore, the springs on the medial plantar artery can may have a spring constant of about 0.8 N/mm. Indeed, those in the art may adjust those values to accommodate different requirements (e.g., 10-20% range above, below, or both above and below the noted values). In some embodiments, the spring force may be between about 0.5 N or 1 N to about 10 N, or the spring force may be between about 1 N to about 5 N.

Figure 3A:
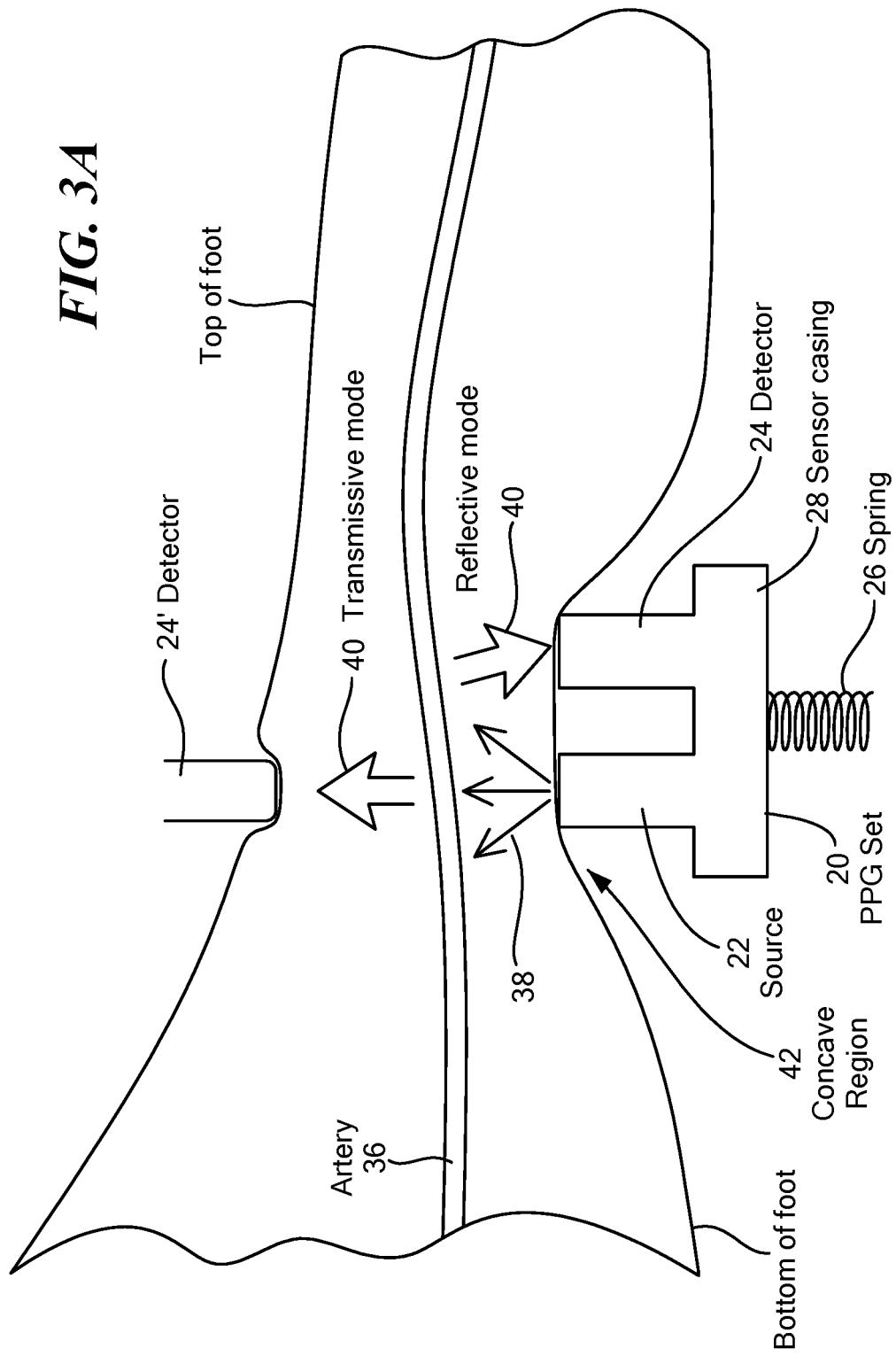

FIG. 3A schematically shows a cross section of a foot while PPG measurements are being performed. A PPG set 20 is shown with a light source 22 and a detector 24 side-by-side next to each other. They are mounted on an upper surface of a sensor casing 28, and a spring 26 is shown coupled to a lower surface of the sensor casing 28. The spring 26 is coupled to the inner surface of the base (not shown).

The source 22 emits one or more wavelengths of light 38 (e.g., electromagnetic radiation) into the bottom of the foot. The emitted light 38 may include green, red, and/or infra-red light which travels through the tissue of the foot. Some of the emitted light 38 will interact with arteries 36 in the foot. After interacting with the arteries of the foot, some of the light may be detected as detected light 40 by the detector 24 that is adjacent to the source 22, in an operative mode known as a reflective mode. Furthermore, after interacting with the arteries 36 of the foot, some of the detected light 40 may be detected by a detector 24 that is opposite the source, at the top surface of the foot, in an operative mode known as a transmissive mode.

The detectors 24 measure the magnitude of the amount of the detected light 40 that is gathered by the detector 24 as a function of a time that the measurements (e.g., tests) are conducted, and they produce a pulse signal that comprises an AC (pulsatile) and a DC (slowly varying) component. The AC component is attributed to changes in the blood volume synchronous with each heartbeat, whereas the DC component is related to respiration, tissues, and average blood volume. AC amplitude represents the strength of the arterial pulsation, and a large AC amplitude indicates strong arterial pulsation.

As shown, the PPG set 20 may protrude into the skin of the foot such that the PPG set 20 forms a temporary concave region 42 in the skin of the foot. The concavity 42 shown in FIG. 3A may exaggerate the size of the concave region 20, as it is not intended to be drawn to scale, but to illustrate a concave effect. As noted, the spring 26 provides sufficient bias (force) to make a firm contact with the surface of the foot, but not so much force as to attenuate the blood flow in region being measured in the artery 36. That is, the spring tension (e.g., bias) is tuned to be able to hold the PPG sets 20 with optimal bias against the skin to detect blood volume changes in the microvascular bed of the plantar tissue without substantially effecting the blood flow changes.

As discussed above, measuring detected light 40 in the "reflective mode" of PPG detection involves having the light source 22 and the detector 24 side-by-side on the sensor casing 28. This embodiment is useful in an open platform (discussed below) when the light source 22 and the detector 24 are facing the skin from the same direction, as illustrated by the PPG set 20 in FIG. 3A. Moreover, this reflective mode may also be useful in a closed platform (discussed below), such as a shoe or foot fixture to receive the foot.

Alternatively, rather than use reflective mode with an adjacent or nearby detector, the emitted light 38 that enters the skin and passes through the artery 36 may be measured as detected light 40 by a detector 24' opposite from the light source 22; in this example, a detector 24' on the top of the foot, which may be considered to be operating in a "transmissive mode" of PPG detection. In addition to being useful in an open platform, this embodiment also may be particularly useful in a closed platform when the light source 22 and the detector 24 are facing the skin on opposite sides of the foot.

In some embodiments, there may be more than one light source and more than one detector. In particular, some embodiments may include sources providing light (e.g., electromagnetic radiation) of one or more wavelengths. One example uses a green light source and an infra-red (e.g., IR) light source. Green, red, and IR wavelengths have been shown to be useful at extracting pulse rates from users. IR wavelengths have also shown to be suitable for PPG-based measurements, including oxygen saturation determination, such as $SpO_2$. In some embodiments, PPG measurements using a combination of light sources and detectors operating simultaneously with multiple wavelengths, such as the red and IR wavelengths, measures $SpO_2$.

FIG. 3B schematically illustrates the potential effects of spring bias on the measurement of the arterial flow. As shown, three PPG sets are mounted on springs and are shown extending against the bottom of a foot. A curved arrow loop representing a light signal is shown being emitted from the source and detected by the detector. An artery is also shown.

The left PPG set is contacting the skin, but is not protruding into the bottom of the foot and thus, is not causing a concave region. In this example, the light is not interacting very strongly with the subcutaneous blood flow, and the AC signal likely would be weak.

The middle PPG set is protruding into the bottom of the foot, but is not protruding into the artery. In this example, the light is interacting very strongly with the artery, and the AC signal would be strong. AC amplitude represents the strength of the arterial pulsation, and a large AC amplitude indicates strong arterial pulsation. With each heart beat there are force vectors which project outward against the blood vessel walls in a radial direction (normal force vectors). The resultant force in the vertical direction is the sum of all vertical force components of the normal force vectors.

The right PPG set is protruding into the bottom of the foot and is protruding into the artery. In this example, the blood flow may be attenuated and the AC signal would be weaker. As such, the contacting force exerted on the photoplethysmographic (e.g., PPG) sensor is too high, causing the arterial wall to begin to flatten. As the result of compression, the external pressure caused by the contacting force from the PPG set approaches the intra-arterial pressure. The difference between the intra-arterial pressure and external pressure is defined as transmural pressure, and when the transmural pressure decreased the blood flow, and therefore the AC component of the PPG signal, is attenuated.

From the viewpoint of the arterial wall properties, the AC amplitude increases as the contacting force increases up to a certain point, as exemplified by the middle PPG set, where the transmural pressure goes to zero. After that peak point, the AC amplitude decreases since the artery begins to be occluded, as exemplified by the right PPG set. Eventually, the artery is pushed against bone and other tissue, and the distal arterial wall will eventually flatten completely and the pulsation will disappear.

Figure 3C:
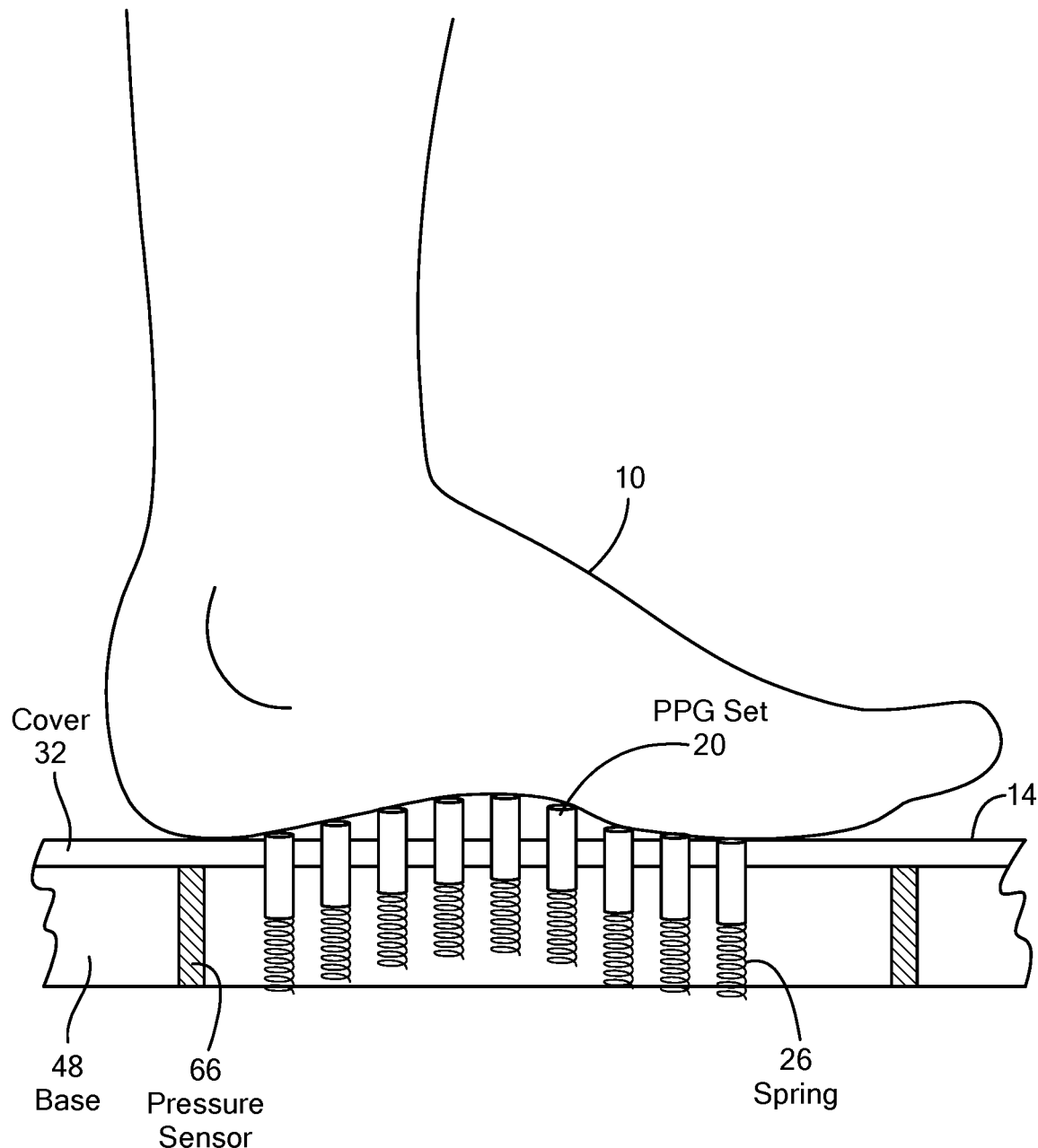

FIG. 3C schematically illustrates one embodiment of an open platform configured to perform PPG measurements.

The open platform includes a cover 32 having a platform contact surface 14. PPG sets protrude above the platform contact surface (aka the "top surface") through holes and contact/abut the bottom surface of a foot 10. The top contact surface of each of the PPG sets is pressed against the bottom surface of the foot at different heights relative to the cover contact surface based on the shape of the foot. For example, one or more PPG sets contact the arch of the foot farther away than the location where one or more PPG sets contact the heel of the foot. In locations where the skin of the foot may actually protrude into the through hole in the platform contact surface 14 of the rigid platform, such as at the heel of the foot, the top contact surface of a PPG set will come into contact with the skin of the foot a distance below the contact surface of the rigid platform.

The spring 26 between the bottom of the PPG set 20 and the inner surface of the base 48 is configured to produce a biasing force that brings the top contact surface of the PPG set 20 into contact with skin of the foot 10 regardless of whether the skin is above the contact surface of the rigid platform (such as with the arch) or below the contact surface 14 of the rigid platform (such as with the heel).

The bias provided by the spring 26 does not depend on the weight (e.g., mass) of the person on the rigid platform 16. Whether the user is large or small, standing, sitting, or lying down, as long as a portion of the foot 10 of the user is in contact with the contact surface 14 of the rigid platform, the springs 26 will apply a bias force sufficient to take PPG measurements with each PPG set 20. Accordingly, this bias forced is independent of the force that the foot 10 applies to the top surface of the platform.

In some embodiments, the rigid platform 16 includes one or more pressure sensors 66, as shown in FIG. 3C. These pressure sensors 66 provide a signal to a placement system configured to start analyzing a foot 10 in response to measurements of the pressure sensor 66. Furthermore, a measurement of the pressure sensor 66 may be combined with a measurement of at least one PPG set 20 to initiate analysis of one or both feet of the user.

Figure 3D:
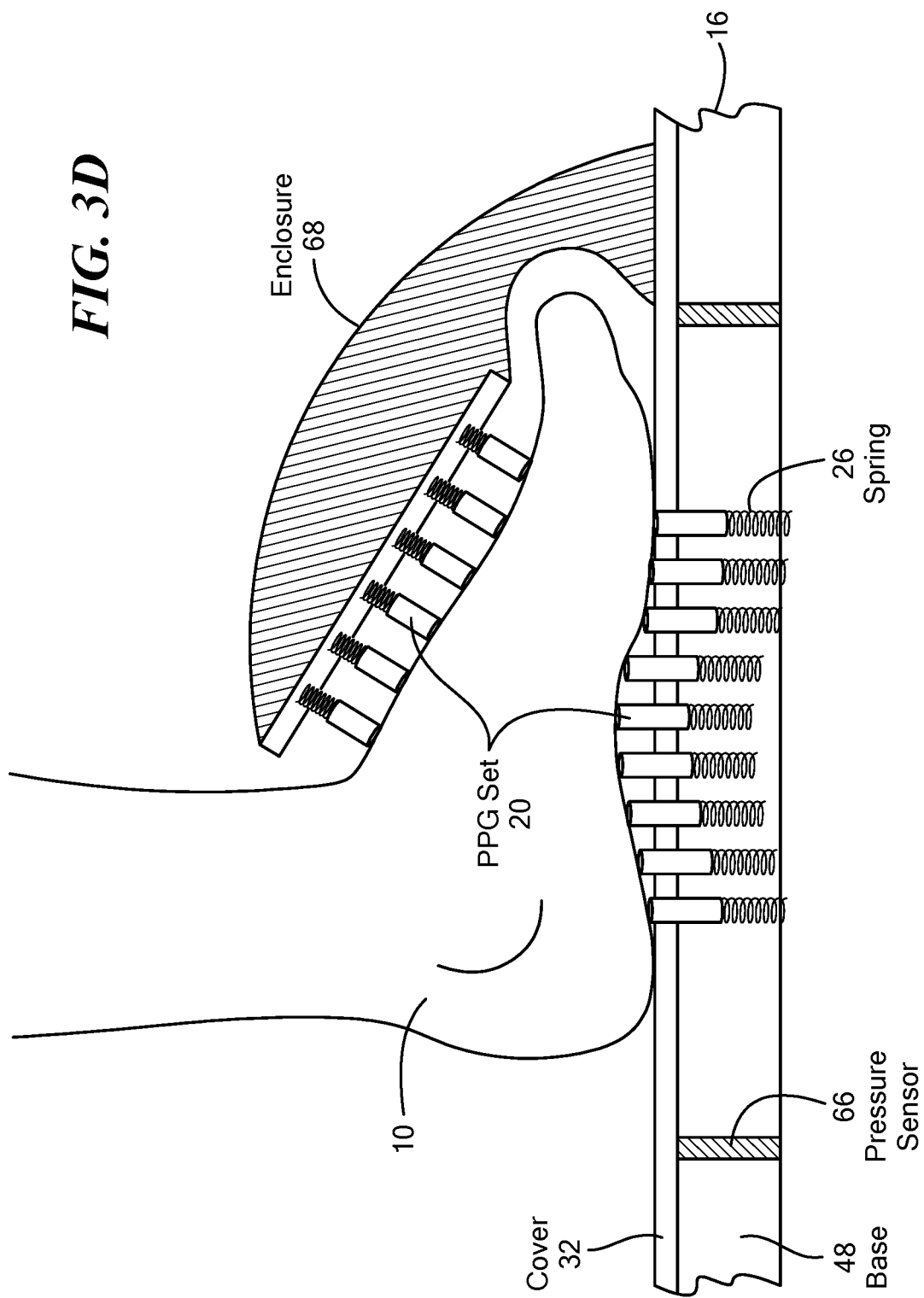

FIG. 3D schematically illustrates one embodiment of a closed platform to perform PPG measurements. In this embodiment, an enclosure 68 is provided as a part of the platform 16 to bring PPG sets 20 and/or detectors 24 into contact with the top and/or sides of a 10 foot. As shown in the embodiment of FIG. 3C, the cover 32 and the base 48 of the closed platform are substantially similar to the open platform. That is, the rigid platform includes at least PPG sets 20, springs 26, and pressure sensors 66. In addition, the closed platform also encloses one or both feet of the user with the enclosure 68 that is attached to, or part of the rigid platform. The closed platform may be manufactured as a single unit, or it may be assembled from several parts.

In some embodiments, the closed platform may operate in a transmissive mode, in a reflective mode, or both simultaneously. By having detectors 24 located on the inside surface of the enclosure 68, it is possible for a light source 22 in the rigid platform to transmit light of a wavelength through the foot and have its intensity measured by the detector located on the inside of the enclosure 68.

In some embodiments, the PPG sets 20 and/or detectors 24 are mounted in the enclosure 68 in a manner analogous with how they are mounted in the rigid platform 16. That is, the PPG sets 20 and/or detectors 24 are mounted on springs 26 with a similar bias as described for the springs 26 in the rigid open platform. Furthermore, the PPG sets and/or detectors move normal or not-normal to the platform surface (e.g., like plungers) through openings in a contact surface of the enclosure. Furthermore, in some embodiments, the PPG sets 20 mounted in the enclosure 68 take PPG measurements in substantially the same manner that the PPG measurements are taken by PPG sets 20 in the rigid platform 16.

Of note is the fact that this embodiment of FIG. 3D takes readings from another part of the foot 10—the top of the foot—not necessarily the plantar portion. In fact, some embodiments may take measurements from the side of the foot. Accordingly, discussion of just taking measurements from the bottom of the foot is for exemplary purposes only and not intended to limit all embodiments.

The measurements in the foot may be used to detect irregularities in the blood flow indicative of early stages of the formation of a foot ulcer. Generally speaking, an ulcer is an open sore on a surface of the body generally caused by a breakdown in the skin or mucous membrane. Diabetics often develop foot ulcers on the soles of their feet as part of their disease. In this setting, foot ulcers often begin as a localized inflammation or infection (e.g. as a pre-ulcer, which has not broken through the skin but exhibits an elevated temperature) that may progress to skin breakdown and infection.

It should be noted that discussion of diabetes and diabetics is but one example and used here simply for illustrative purposes only. Accordingly, various embodiments apply to other types of diseases (e.g., stroke, deconditioning, sepsis, friction, coma, etc.) and other types of ulcers—such embodiments may apply generally where there is a compression or friction on the living being's body over an extended period of time. For example, various embodiments also apply to ulcers formed on different parts of the body, such as on the back (e.g., bedsores), inside of prosthetic sockets, or on the buttocks (e.g., a patient in a wheel chair). Moreover, illustrative embodiments apply to other types of living beings beyond human beings, such as other mammals (e.g., horses or dogs). Accordingly, discussion of diabetic human patients having foot ulcers is for simplicity only and not intended to limit all embodiments of the invention.

The approach described here is useful in improving patient compliance in measuring blood flow in affected areas of the body. If a diseased or susceptible patient does not regularly check his/her feet, then that person may not learn of an ulcer or a pre-ulcer until it has emerged through the skin and/or requires significant medical treatment. Accordingly, illustrative embodiments implement an ulcer monitoring system in any of a variety of forms—preferably in an easy to use form factor that facilitates and encourages regular use.

Figure 4A:
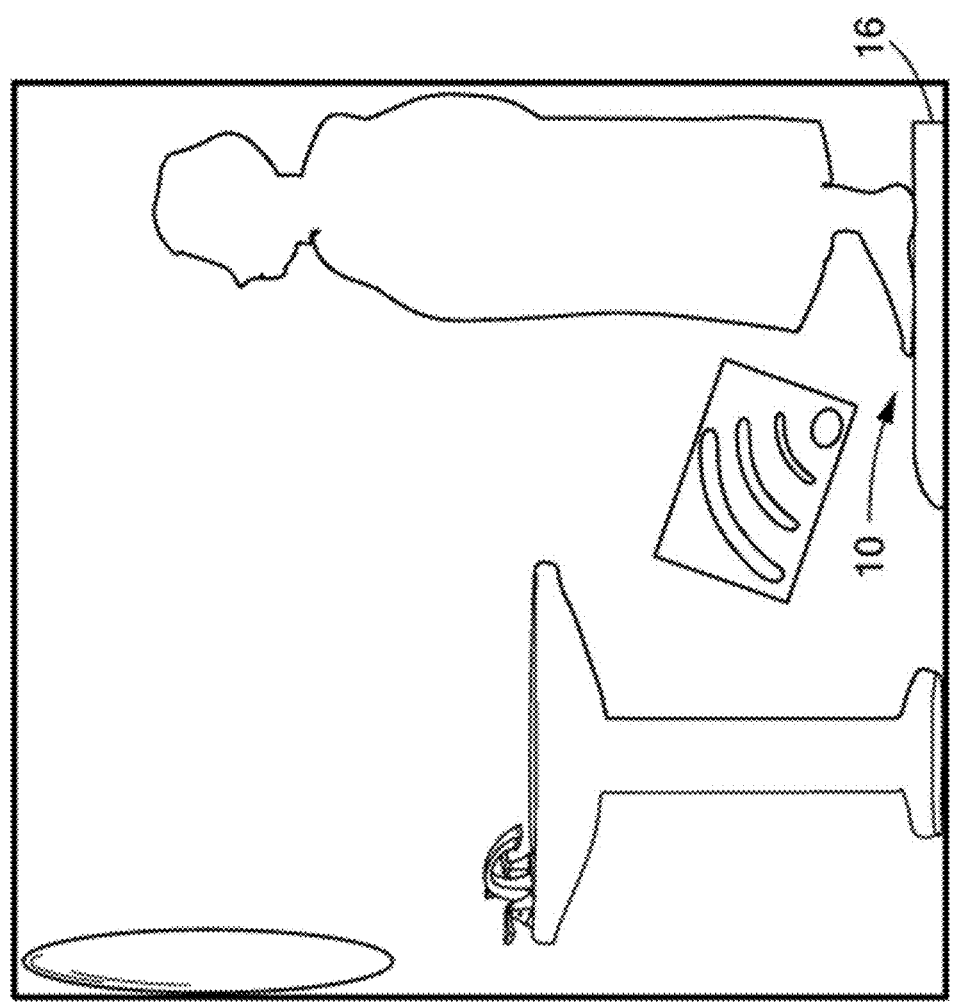
Figure 4B:
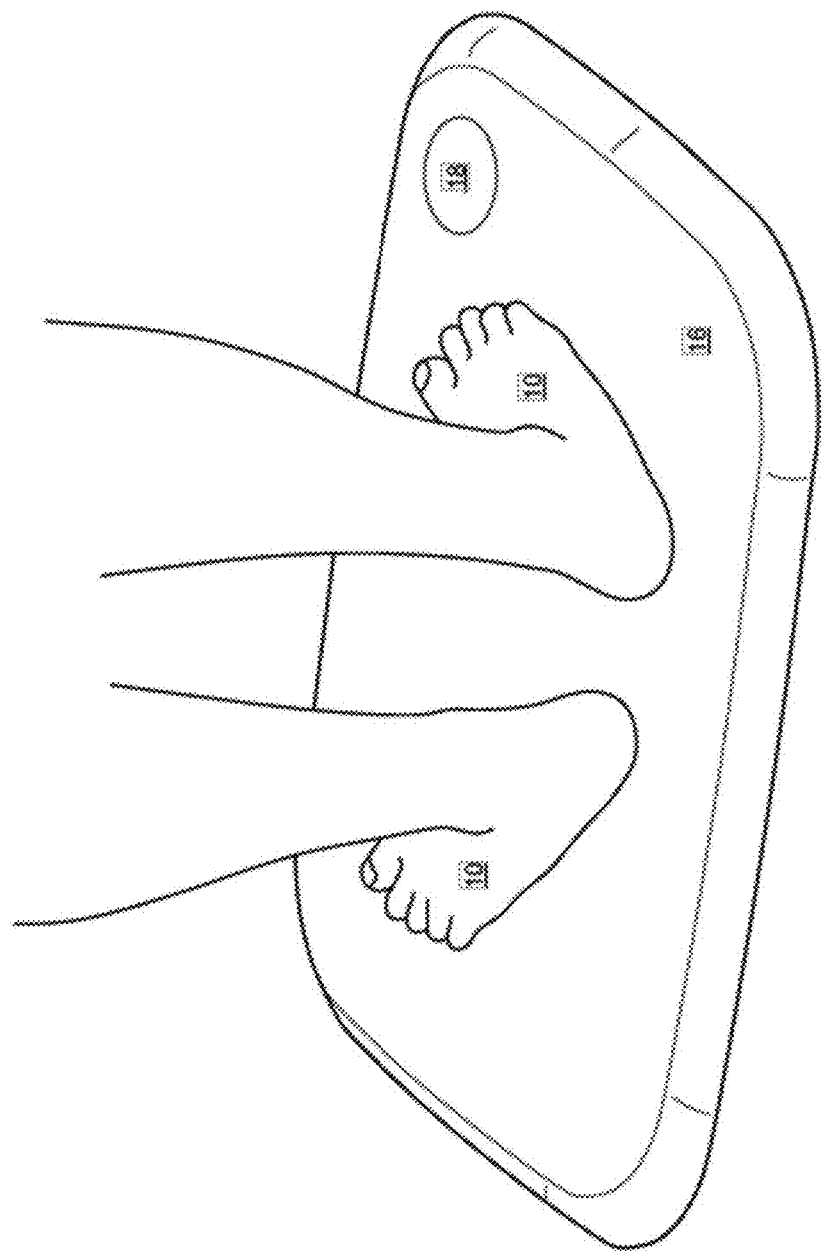

FIGS. 4A and 4B schematically show one form factor, in which a patient/user steps on an open platform 16 that gathers data about that user's feet 10. In this particular example, the open platform 16 is in the form of a floor mat placed in a location where he the patient regularly stands, such as in front of a bathroom sink, next to a bed, in front of a shower, on a footrest, or integrated into a mattress. As an open platform 16, the patient simply may step on the top sensing surface of the platform 16 to initiate the process. Accordingly, this and other form factors favorably do not require that the patient affirmatively decide to interact with the platform 16. Instead, many expected form factors are configured to be used in areas where the patient frequently stands during the course of their day without a foot covering. Alternatively, the open platform 16 may be moved to directly contact the feet 10 of a patient that cannot stand. For example, if the patient is bedridden, then the platform 16 may be brought into contact with the patient's feet 10 while in bed.

A bathroom mat or rug are but two of a wide variety of different potential form factors. Others may include a platform 16 resembling a scale, a stand, a footrest, a console, a tile built into the floor, or a more portable mechanism that receives at least one of the feet 10. The implementation shown in FIGS. 4A and 4B has a top surface area that is larger than the surface area of one or both of the feet 10 of the patient. This enables a caregiver to obtain a complete view of the patient's entire sole, providing a more complete view of the foot 10.

The open platform 16 also has some indicia or display 18 on its top surface they can have any of a number of functions. For example, the indicia can turn a different color or sound an alarm after the readings are complete, show the progression of the process, or display results of the process. Of course, the indicia or display 18 can be at any location other than on the top surface of the open platform 16, such as on the side, or a separate component that communicates with the open platform 16. In fact, in addition to, or instead of, using visual or audible indicia, the platform 16 may have other types of indicia, such as tactile indicia/feedback, our thermal indicia.

Rather than using an open platform 16, as noted above, alternative embodiments may be implemented as a closed platform, such as a shoe or sock that can be regularly worn by a patient, or worn on an as-needed basis. For example, the insole of the patient's shoe or boot may have the functionality for detecting the emergence of a pre-ulcer or ulcer, and/or monitoring a pre-ulcer or ulcer.

To monitor the health of the patient's foot (discussed in greater detail below), the platform 16 of FIGS. 4A and 4B gathers PPG data about a plurality of different locations on the sole of the foot 10. This PPG data provides the core information ultimately used to determine the health of the foot 10.

Various Embodiments of the PPG Measurement Implementations

Figure 5A:
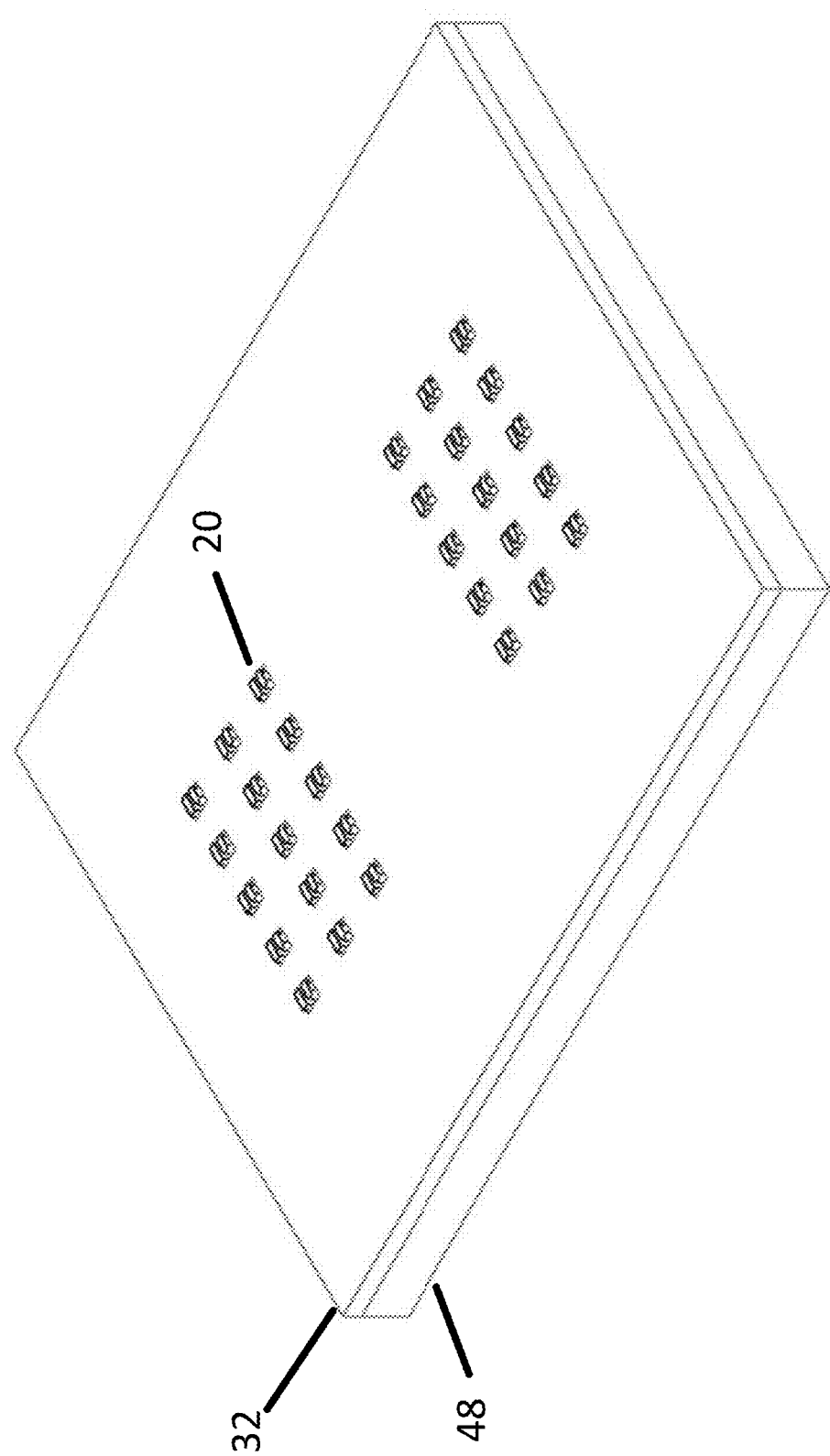

FIG. 5A schematically shows an isometric view of one embodiment of open platform 16. Of course, this embodiment is but one of a number of potential implementations and, like other features, is discussed by example only.

As shown, the platform 16 is formed as a stack of functional layers sandwiched between a cover 32 having a top surface to support the foot, and a rigid base 48. Some of those functional layers may provide physical support, intelligence/logic (e.g., circuitry), among other things. PPG sets 20 are shown extending above the top cover 32 via the through holes. For safety purposes, the base 48 preferably has rubberized or has other non-skid features on its bottom side. The platform 16 preferably has relatively thin profile to avoid tripping the patient and making it easy to use.

To measure blood flow on the bottom of the feet, the platform 16 has an array or matrix of PPG sets 20 fixed in place directly underneath the cover 20. More specifically, the PPG sets 20 are positioned in recesses/apertures in the surface of the base. The PPG sets 26 preferably are laid out in a two-dimensional array/matrix with a relatively small pitch or distance between the different PPG sets 20. As shown, this array may be in two discrete areas—one for each foot, or across a larger area taking up substantially the entire top surface.

In some embodiments, the array of PPG sets 20 may include temperature sensors which may include temperature sensitive resistors (e.g., printed or discrete components mounted onto a circuit board), thermocouples, fiberoptic temperature sensors, or a thermochromic film. Accordingly, when used with PPG sets 20 that require direct contact, illustrative embodiments form the cover 26 with a thin material having a relatively high thermal conductivity. The platform 16 also may use temperature sensors that can still detect temperature through a patient's socks.

As discussed in greater detail below and noted above, regardless of their specific type, the plurality of PPG sets 20 generate a plurality of corresponding blood flow data values for a plurality of portions/spots on the patient's foot 10 to monitor the health of the foot 10. Furthermore, temperature data gathering sensors may be included in the platform 16, and the subsequent temperature data may be included with the PPG data in the analysis of the health of the user's foot.

Some embodiments also may use pressure sensors for various functions, such as to determine the orientation of the feet 10 and/or to automatically begin the measurement process. Among other things, the pressure sensors may include piezoelectric, resistive, capacitive, or fiber-optic pressure sensors. The platform 16 also may have additional sensor modalities beyond PPG sets, temperature sensors, and pressure sensors, such as positioning sensors, GPS sensors, accelerometers, gyroscopes, and others known by those skilled in the art.

Figure 5B:
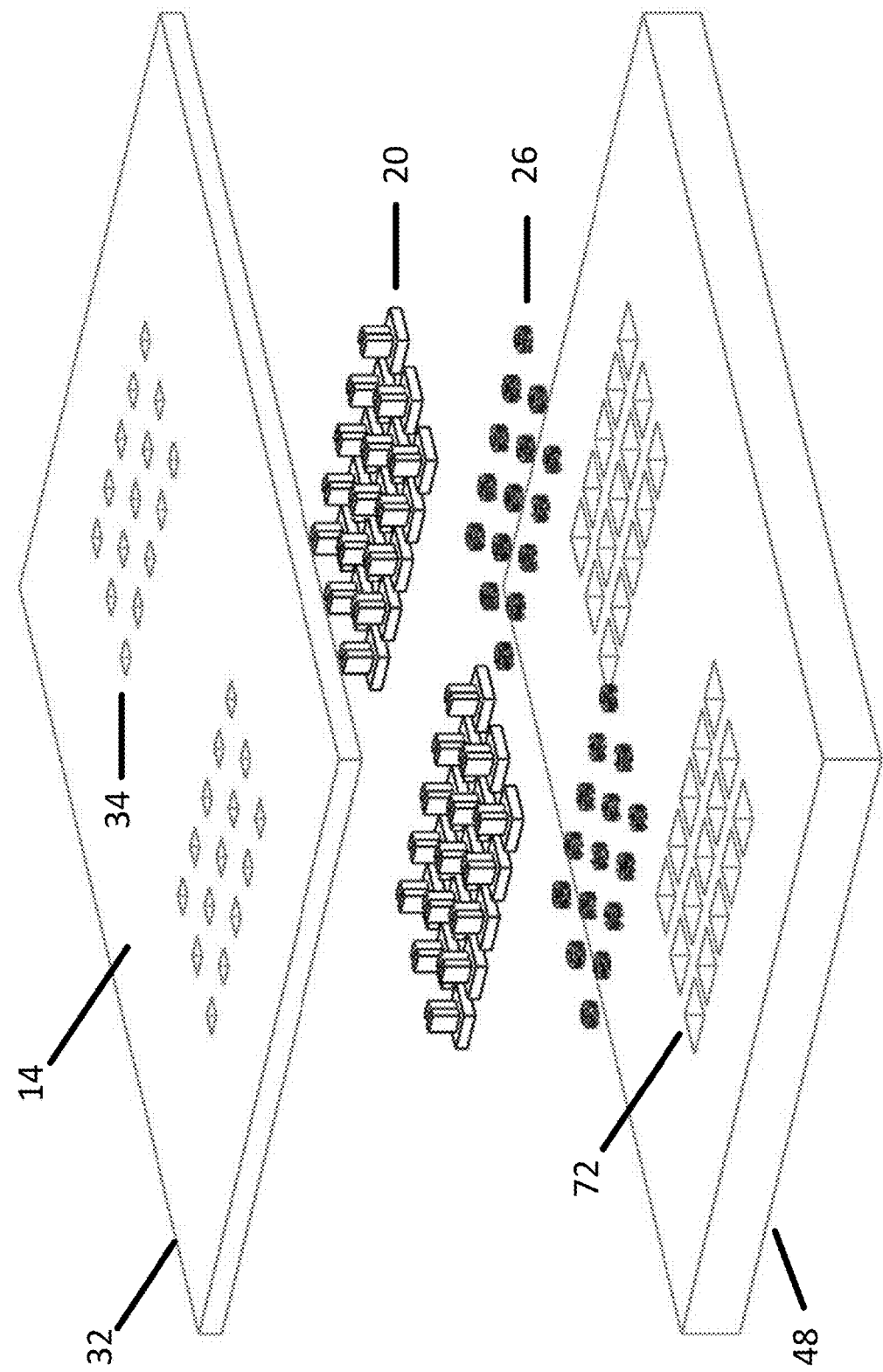

FIG. 5B shows an exploded view of the open platform 16 shown in FIG. 5A. This figure shows the rigid base 48 separated from the cover 32, and the PPG sets 20/springs 26 aligned with their prescribed apertures 34 in the cover 32 and recesses 72 in the base. Accordingly, this figure more clearly shows how each PPG set 20 has an associated spring 26 coupled at one end to the bottom of the recess 72 in the rigid base 48 and at the other end to the bottom of the PPG set 20. Each PPG set 20 extends through the cover 32 and is configured to move upwardly and downwardly, in a direction normal to the platform surface 14 (i.e., in the Z-direction) within and outside of its aperture 34. While this one-directional motion may be substantially perpendicular to the x-y plane of the top surface 14 of the cover 32, some embodiments also may make this movement move at an angle to the top surface 14. For example, to contact portions of the foot that are angled, one or more of the PPG sets 20 may be oriented at an angle. Each PPG set 20 moves on its own spring 26 independently of the movement of the other PPG sets 20 so that the plurality of PPG sets array can conform to the shape of the bottom of a user's foot.

The PPG sets may be movably coupled in a manner that enables the sensor to move up and down through the hole as pressure/force (normally from the user's foot) is applied. Depending on the location of the user's foot, the spring heights and strengths can be preconfigured to achieve the best signal possible. For example, one or more springs may be nominally set so that the top of their PPG sets normally (i.e., before foot force is applied) between about 5 mm to 10 mm above flush with the top surface of the open platform to target the deep plantar artery, about 10 mm to about 20 mm above flush to target the medial plantar artery, and/or about 7 mm to 15 mm above flush to target the lateral plantar artery. Springs on the deep plantar artery and lateral plantar artery can be configured to a variety of dimensions, including 0.8×9.5×20 mm with a spring constant of 1.067 N/mm. Furthermore, the springs on the medial plantar artery can include dimensions of 0.6×9.5×10 mm with a spring constant of 0.789 N/mm. Indeed, those in the art may adjust those values to accommodate different requirements (e.g., 10-20% range above, below, or both above and below the noted values).

Figure 5C:
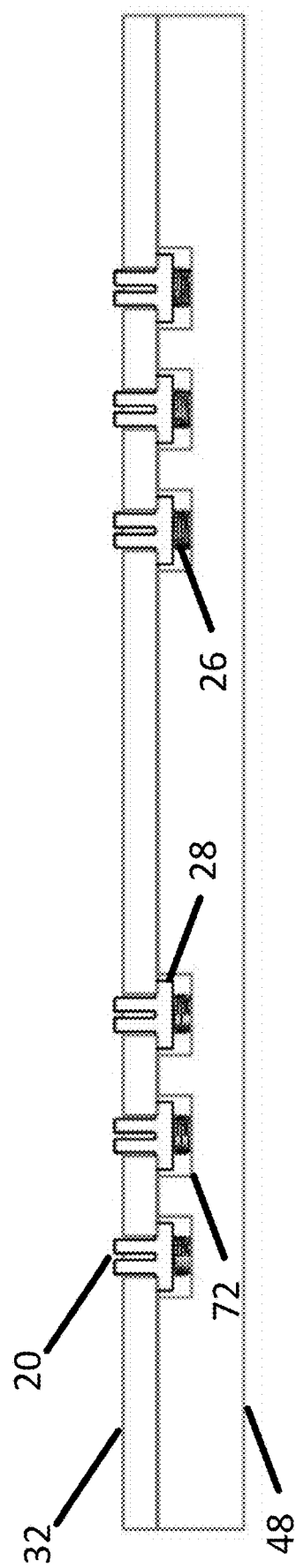

FIG. 5C shows a cross sectional view of the open platform 16 shown in FIGS. 5A and 5B. As shown in FIG. 5B, the spring 26 for each PPG set 20 is coupled, at one end, to the bottom surface of the recess 72 and, at the other end, to the bottom surface of the PPG set 20. The PPG set 20 is positioned in the aperture 34 with the top contact surface of light source and the detector extending through the through hole 34 in the cover to normally be positioned above the top surface 14 of the cover 32. This figure shows one embodiment of the PPG casing 28, which at least partially encases the light source and detector. As shown, the PPG casing 28 has an integrated stop to set a maximum outward distance the PPG set 20 can traverse away from the top surface 14. The geometry of this stop portion is configured to ensure the top surface of the PPG set is appropriately positioned. Moreover, the spring 26 is biased and selected so that it applies sufficient force to ensure that when at rest (i.e., when not receiving a downward force), the stop abuts the corresponding surface of the aperture shown in this figure.

Figure 6A:
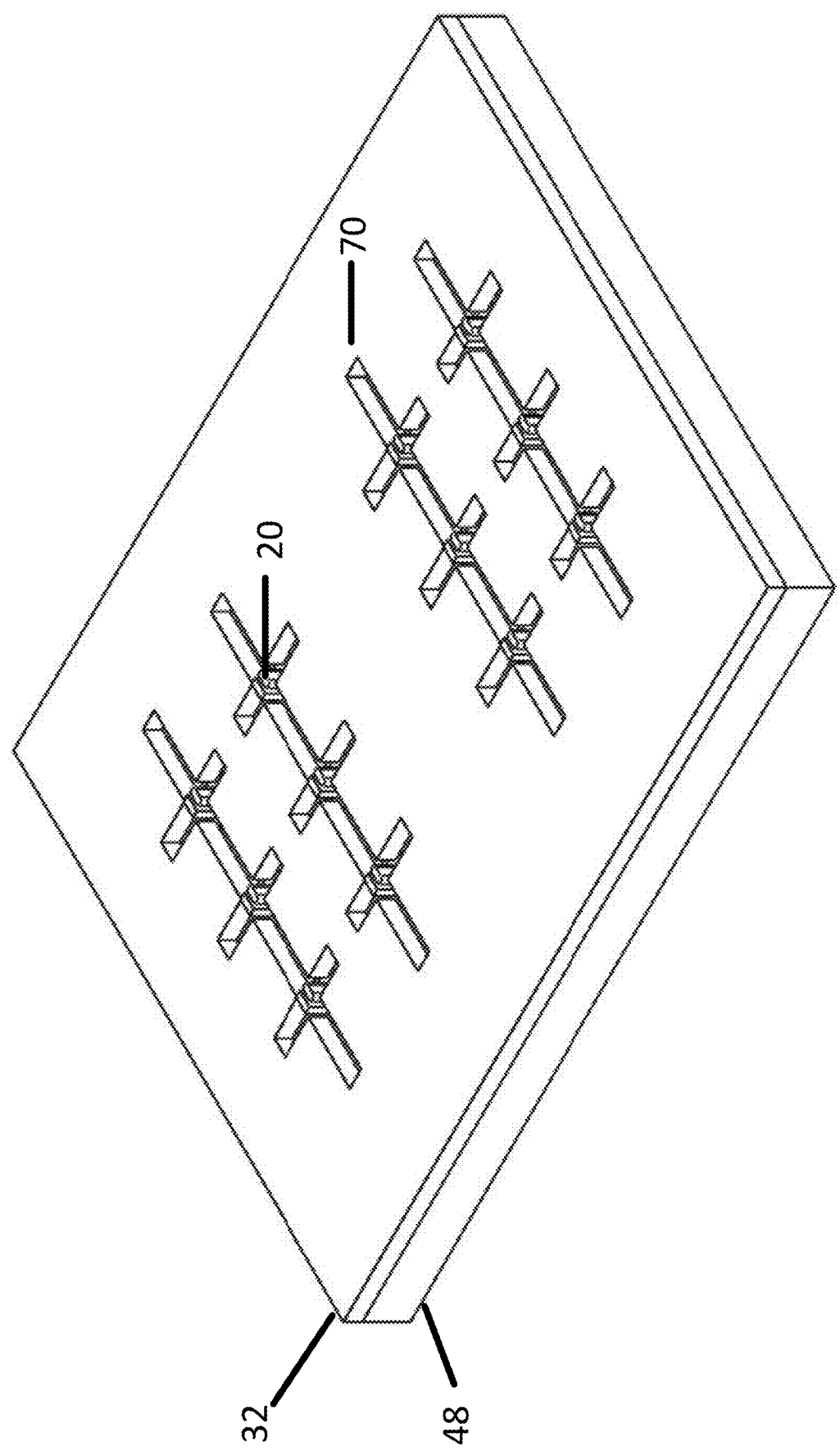

FIG. 6A schematically shows an isometric view of another embodiment of open platform 16. Of course, this embodiment is but one of a number of potential implementations and, like other features, is discussed by example only.

Unlike the embodiment of FIGS. 5A-5C, the cover of this embodiment has through trenches 70 that, together with the apertures of a plurality of other PPG sets, form one aperture. As shown in FIG. 6A, the through trenches 70 have a predetermined pattern that is for illustrative purposes and is not intended to be limitation to the type of patterns that may be used.

Figure 6B:
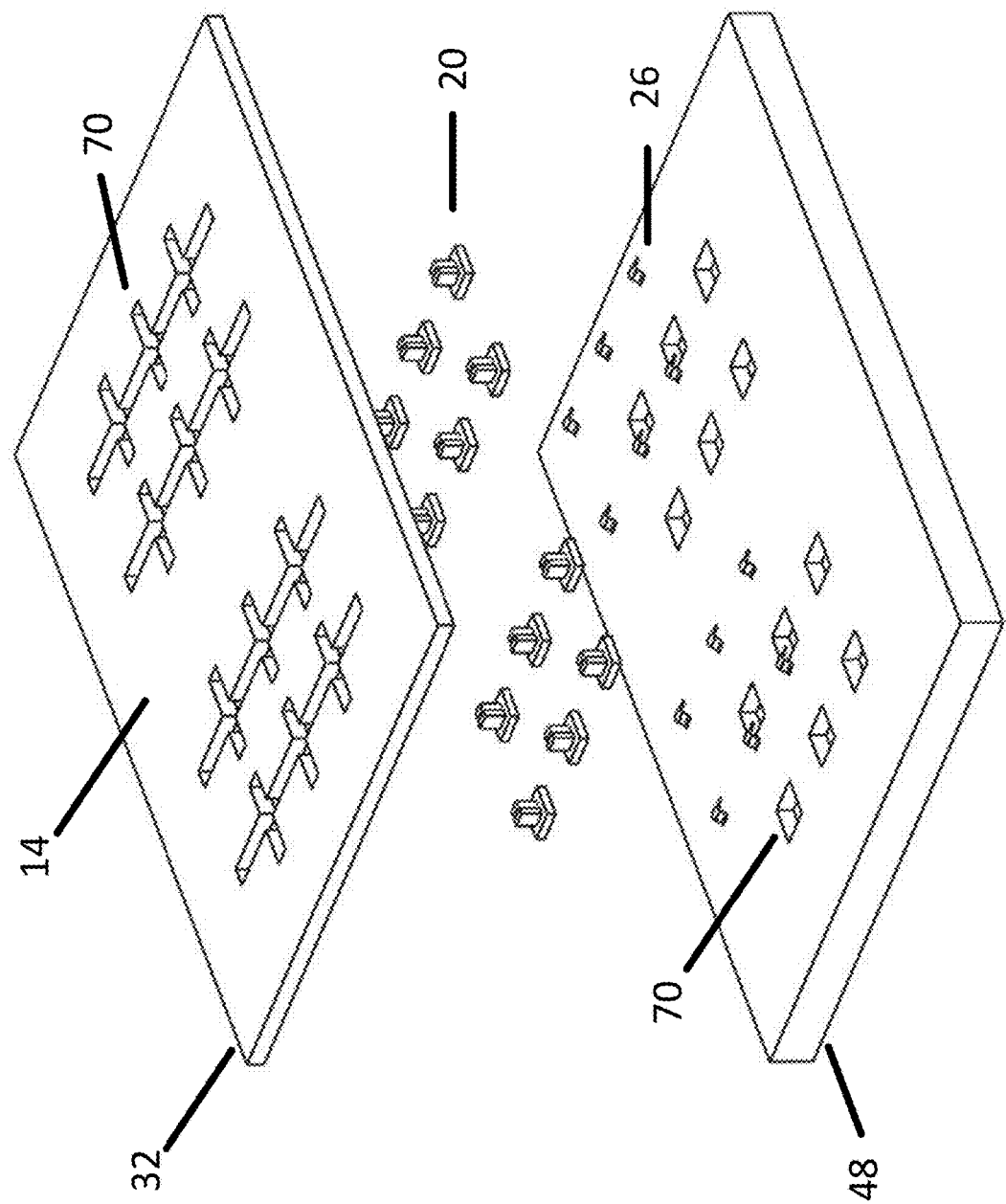
Figure 6C:
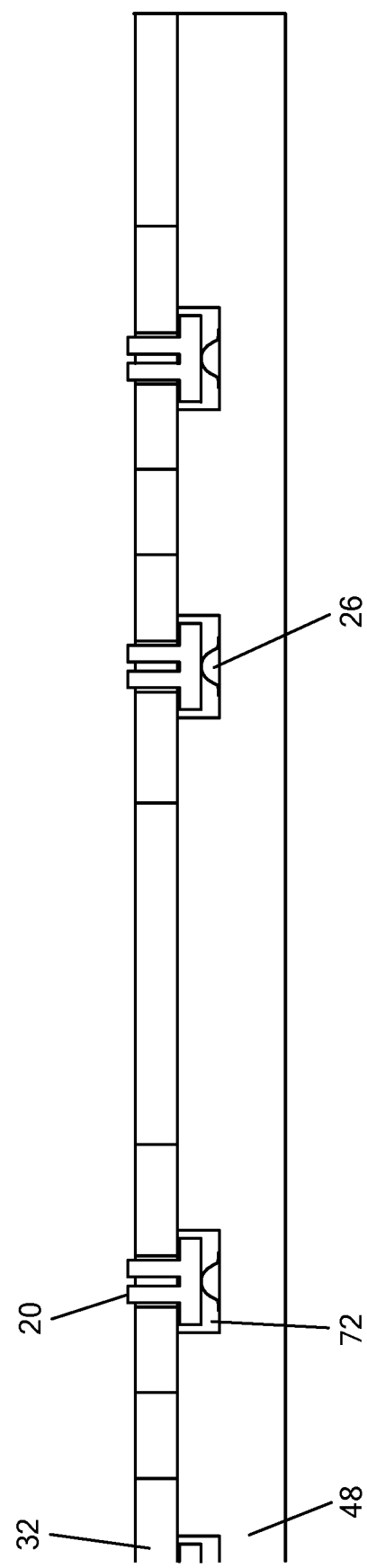

FIG. 6B shows an exploded view of the open platform 16 shown in FIG. 6A. This figure shows how the cover 32 forms the trenches 70, while the rigid base 48 is substantially the same as the embodiment of FIGS. 5A-5C. Further, as shown in FIGS. 6B and 6C, rather than being coil springs, the springs 26 of this embodiment are formed as leaf springs. These and other embodiments may use other types of spring, such as elastomeric springs, cantilever springs, foam springs, and/or viscoelastic springs. Indeed, the springs of the various embodiments discussed herein may apply to other embodiments. For example, the springs of FIGS. 6A-6C may be used in the embodiment of FIGS. 5A-5C.

Figure 7A:
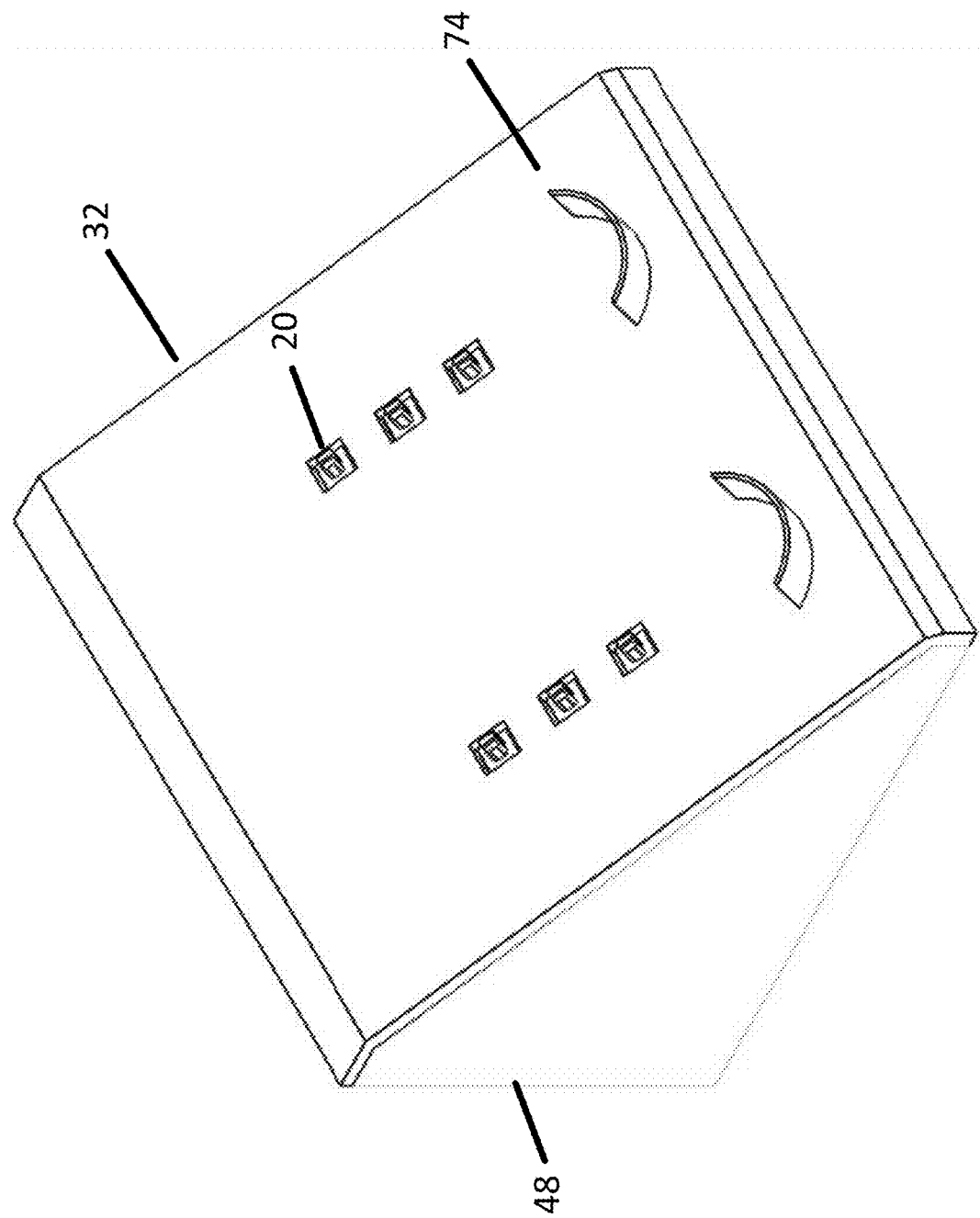
Figure 7C:
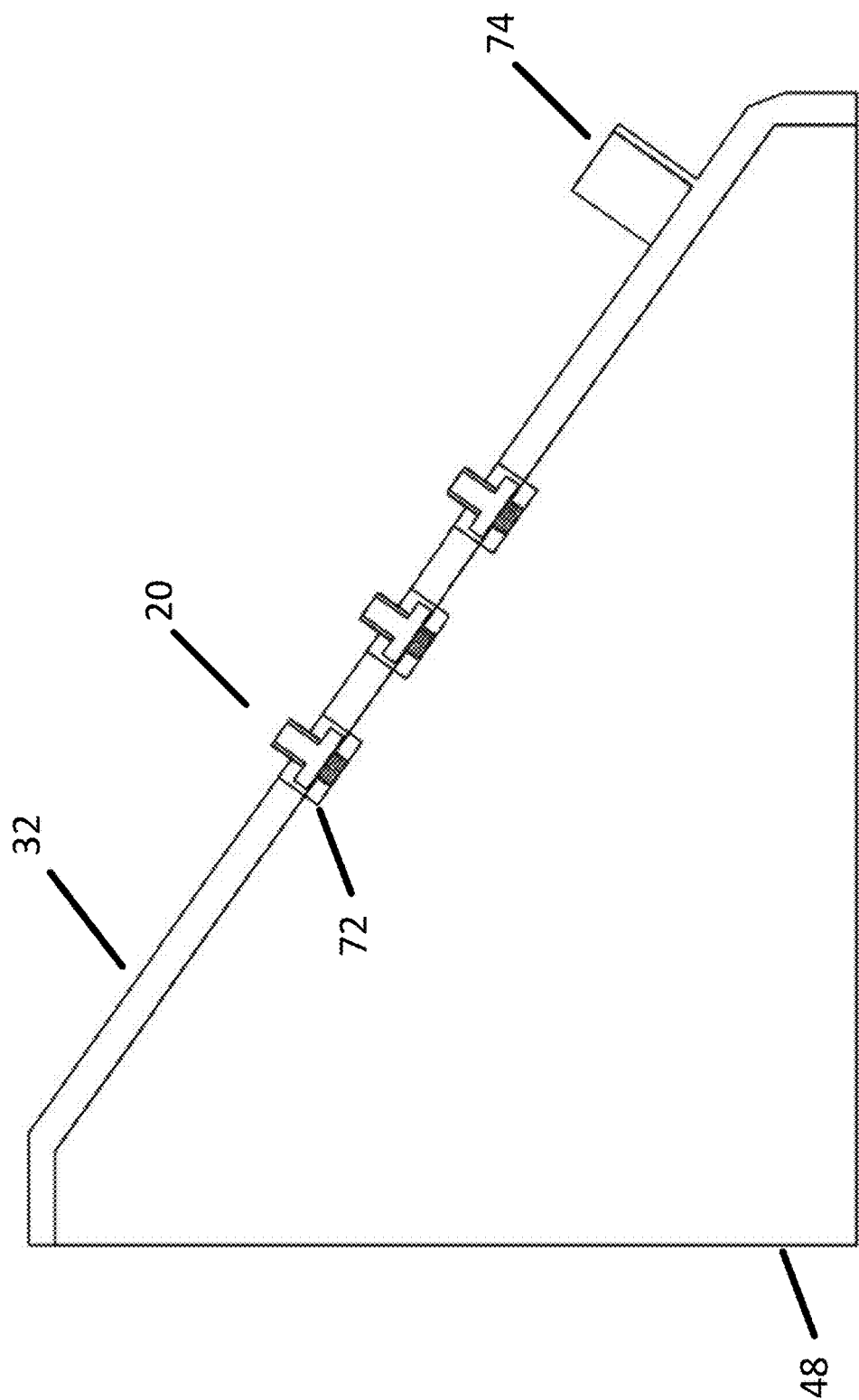

FIGS. 7A-7C schematically show different views of another embodiment of open platform 16. Unlike the above embodiment, the base 48 and cover 32 are configured so that the top surface 14 of the cover 32 is at an angle relative to the bottom of the base 48. This angle may be a generally neutral angle, such as 45 degrees, although it may be another angle between zero degrees and 90 degrees, such as between 10, 20, or 30 degrees and 40, 50, or 60 degrees. This embodiment may be particularly useful when the user is sitting. This embodiment also has guide indicia 74 on the top surface of the cover to help the user in positioning their feet.

As shown, in this embodiment, the indicia 74 is in the form of a curved, relatively flat member intended for the user to use to position their feet. Specifically, during use, the back of the user's heel should contact/abut the large, concave surface of the member to properly align their feet with the PPG sets 20 (to the extent possible). Other embodiments, however, may not curve the members, or even form them with other geometries and sizes. As such, in some embodiments, the indicia 74 may be straight or bumps protruding from the surface. In other embodiments, rather than being raised above the surface, the indicia 74 may be flush with the top surface 14, and/or recessed into the stop surface. For example, the indicia 74 may be a depression in the top surface 14 of the cover 32, or they may be a marking that is substantially in the plane of the top cover 32.

FIG. 7B shows an exploded view of the open platform 16 shown in FIG. 7A. As shown and like the embodiments of FIGS. 6A-6C, the PPG sets 20 and springs of this embodiment are generally mounted and operate in a manner similar to those of FIGS. 5A-5C.

Note that although FIGS. 5A-7C do not explicitly show circuitry layer(s) underlying the PPG sets, various embodiments do have printed circuit boards with circuitry for controlling operation of the overall apparatus. These figures therefore are simplified and not intended to suggest the underlying circuitry is not on-board the platform. As discussed above and below, this circuitry can perform various roles, from PPG energizing, detection management, system control, data storage (e.g., read only memory), networking/communication devices (e.g., modems), etc.

Networking and Data Measurement

Figure 8:
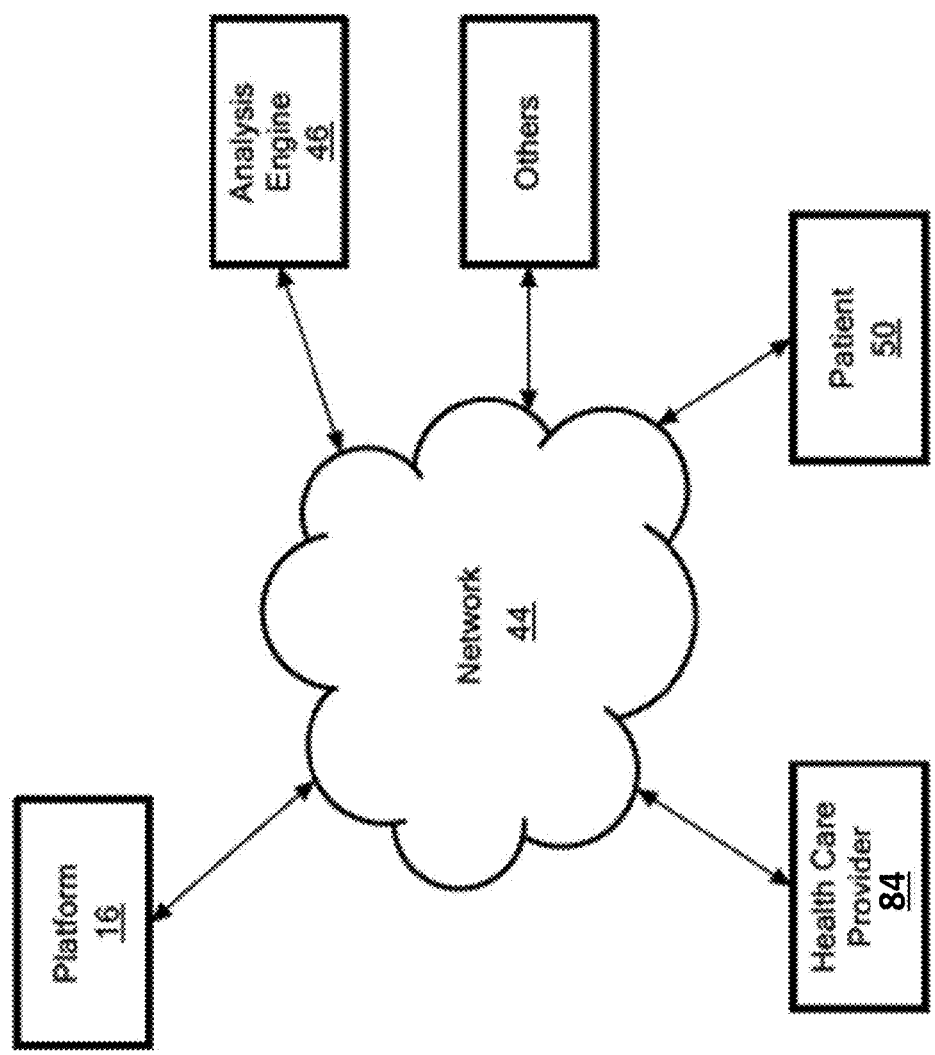

Although it gathers PPG and other data about the patient's foot, illustrative embodiments may locate some or substantially all (or other) logic for monitoring foot health at another location. For example, such additional logic may be on a remote computing device. To that and other ends, FIG. 8 schematically shows one way in which the platform 16 can communicate with a larger data network 44 in accordance with various embodiments the invention. As shown, the platform 16 may connect with the Internet through a local router, through its local area network, or directly without an intervening device. This larger data network 44 (e.g., the Internet) can include any of a number of different endpoints that also are interconnected. For example, the platform 16 may communicate with an analysis engine 46 that analyzes the PPG data and/or thermal data from the platform 16 and determines the health of the patient's foot 10. The platform 16 also may communicate directly with a health care provider 84, such as a doctor, nurse, relative, and/or organization charged with managing the patient's care. In fact, the platform 16 also can communicate with the patient, such as through text message, telephone call, e-mail communication, or other modalities as the system permits.

Figure 9:
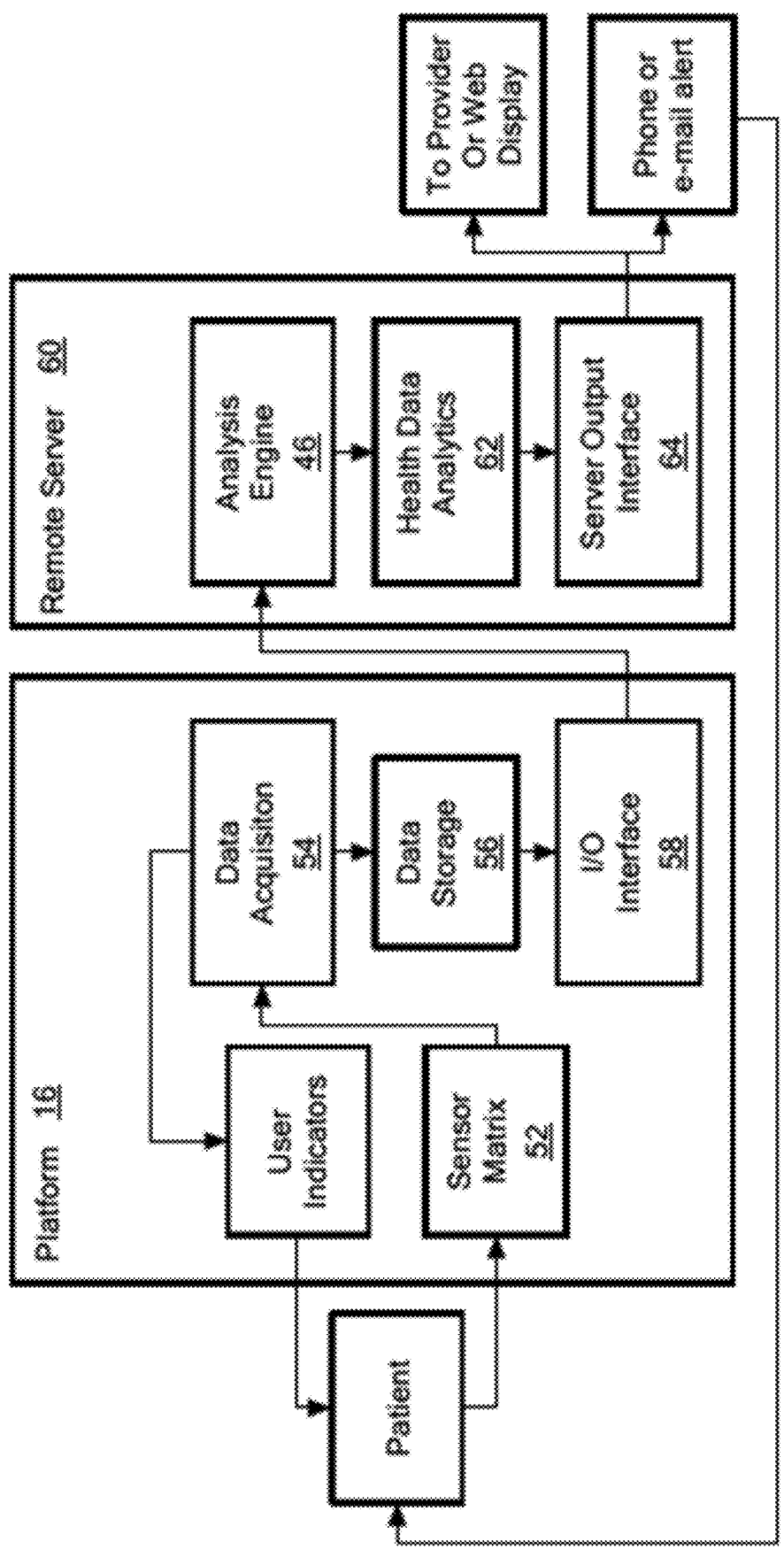

FIG. 9 schematically shows a block diagram of a foot monitoring system, showing the platform 16 and the network 44 with its interconnected components in more detail. As shown, the patient communicates with the platform 16 by standing on or being received in some manner by the array of PPG sets, which is represented in this figure as a "sensor matrix 52." A data acquisition block 54, implemented by, for example, a motherboard and circuitry, controls acquisition of the PPG data and other data for storage in a data storage device 56. Among other things, the data storage device 56 can be a volatile or nonvolatile storage medium, such as a hard drive, high-speed random-access-memory ("RAM"), or solid-state memory. The input/output interface port 58, also controlled by the motherboard and other electronics on the platform 16, selectively transmits or forwards the acquired data from the storage device to the analysis engine 46 on a remote computing device, such as a server 60. The data acquisition block 54 also may control the user indicators/displays 18, which provide feedback to the user through the above mentioned indicia (e.g., audible, visual, or tactile).

Figure 10:
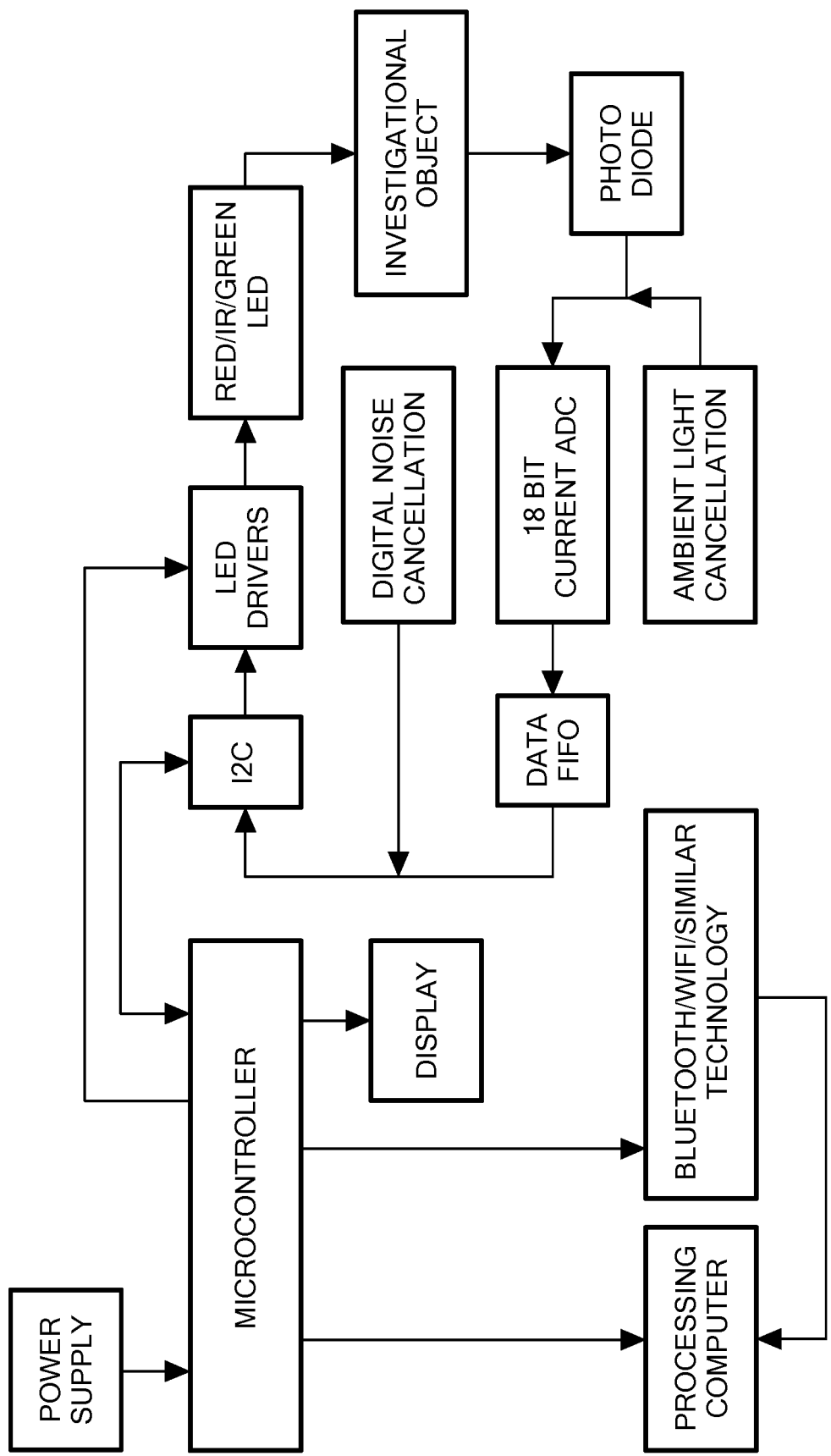

FIG. 10 schematically shows a block diagram of one embodiment of the various components in the platform 16. It should be noted that like other figures, FIG. 10 is a mere schematic representation to facilitate understanding, and each of the components is operatively connected by any conventional interconnect mechanism. In some embodiments, the device of FIG. 10 is integrated into the platform 16 as shown in FIG. 9. In some embodiments the device may be used with a wireless connection (e.g., Bluetooth, 4G, 5G, or WIFI) and a power source instead of direct connection to the remote server 60, or a computing device, such as a personal computer.

Those skilled in the art should understand that each of these components can be implemented in a variety of conventional manners, such as by using hardware, software, or a combination of hardware and software, across one or more other functional components. For example, some functional components may be implemented using a plurality of microprocessors executing firmware. As another example, one or more components may be implemented using one or more application specific integrated circuits (e.g., "ASICs") and related software, or a combination of ASICs, discrete electronic components (e.g., transistors), and microprocessors. Accordingly, the representation of a component as a single box of FIG. 10 is for simplicity purposes only. In fact, in some embodiments, some components may be spread across a plurality of different machines—not necessarily within the same housing or chassis.

Figure 11:
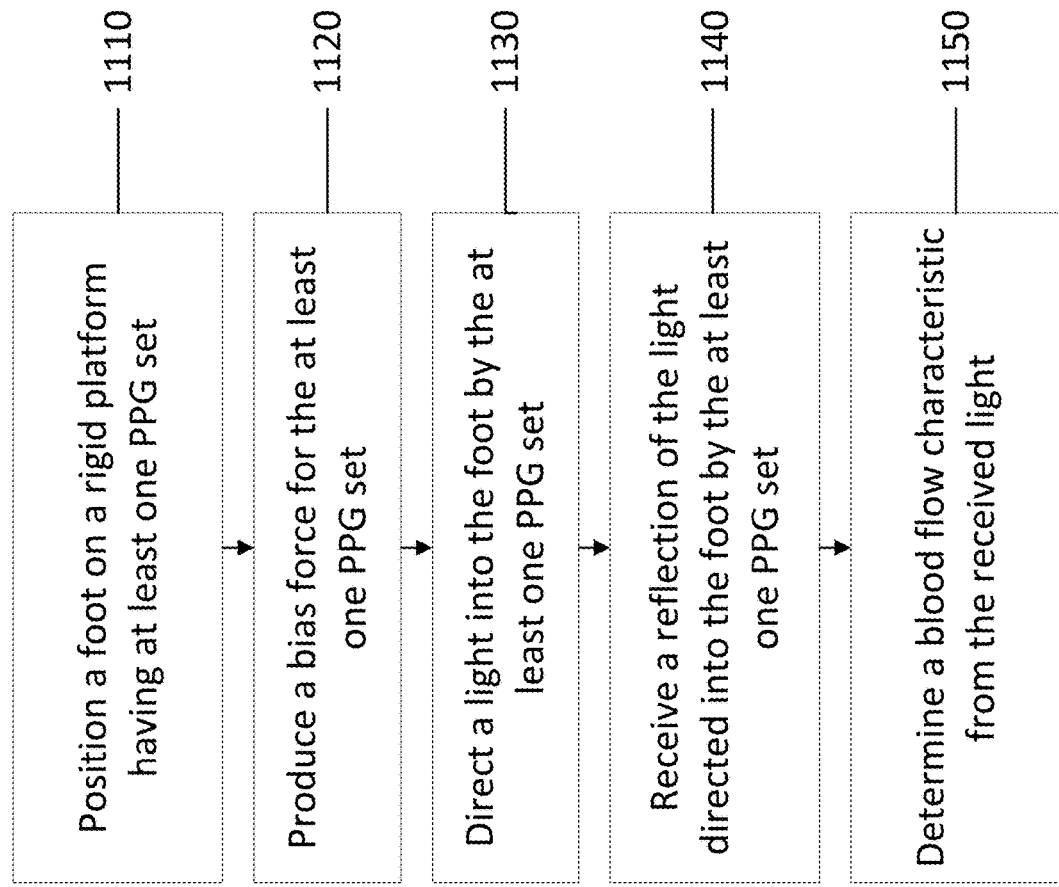
FIG. 11 shows one embodiment of a flow diagram that describes a method of measuring blood flow in a foot.

FIG. 11 shows method of measuring blood flow in a foot in accordance with illustrative embodiments. It should be noted that this method is substantially simplified from a longer process that normally would be used to measure the blood flow. Accordingly, the method may have other steps that those skilled in the art likely would use. In addition, some of the steps may be performed in a different order than that shown, or at the same time. Those skilled in the art therefore can modify the process as appropriate.

The method begins at 1110, in which a foot 10 is positioned on the platform 16 configured like one or more of the above embodiments discussed above. To that end, the user physically brings down the foot, first contacting the top surfaces of the PPG sets 20 and then moving them downwardly (e.g., normal relative to the platform surface) into their apertures 34. By doing so, the foot produces a foot force directed toward the contact surface when positioned on the platform contact surface 14. This foot force overcomes the biasing force the springs 26 apply to their PPG sets 20.

At 1120, when the PPG sets 20 unseat from their biased position against the stops, the foot 10 begins to receive the biasing force. This biasing force preferably is applied to the foot 10 during the some or all of the entire path of each PPG set 20. Specifically, for a given PPG set 20, the foot 10 continues receiving the biasing force until and the foot 10 is supported on the top surface 14 of the platform 16. Preferably, when the foot 10 is supported (whether it is fully or partially supported on the surface 14), the spring 26 of each PPG set 20 (or at least a plurality of the PPG sets) is configured to have excess distance to travel downwardly (from the perspective of the drawings). As such, the spring 26 is not considered to have "bottomed out" against some surface or stop within its aperture 34. Accordingly, when supported on the top surface 14 and the PPG set 20 is relatively static (i.e., no longer moving), the foot receives a consistent biasing force.

In preferred embodiments, this biasing force received by the foot 10 has magnitude that is substantially independent of the foot force—that is the force applied by the foot 10 to the top surface 34 of the platform 16. In other words, the springs 26 and PPG sets 20 are configured so that the weight of the user, the position of the user, the position of the feet 10 on the platform 16, and/or the way the user positions their foot/feet on the top surface 14 (e.g., from a sitting or standing position) has any non-negligible effect on magnitude of the biasing force received by the foot 10. For example, when supported on the platform 16, the foot 10 of a 120 pound user should feel substantially the same biasing force as would a 200 pound user who subsequently uses the same platform 16 (i.e., ensuring the same configurations for the springs 26). In some embodiments, the dynamic biasing force received by the user (i.e., while the net foot force is applied and moving the PPG set 20 downwardly) may vary to some extent depending on the motion and foot force applied, but when static, the foot 10 should receive the biasing force so that the biasing force is independent of the force received by the platform 16/top surface 14. Accordingly, in illustrative embodiments, each PPG set 20 and its corresponding one or more springs 26 are configured so that the biasing force has a magnitude that is substantially independent of the foot force magnitude.

Indeed, as noted, when the user's foot 10 is static on the platform, some PPG sets 20 will be flush with the top surface 14, some will extend outwardly from the top surface 14, and/or some may even be below the top surface 14 (e.g., if the skin of the foot enters the top of the aperture 34).

After producing the biasing force, the process continues to step 1130, in which the light source 22 directs emitted light 38 into the foot 10. Although the light ideally has zero reflection from the outside surface of the foot 10, it is expected that some portion of the emitted light 38 may reflect back and reduce the signal to noise ratio. As discussed below, the light source 22 preferably is configured to abut into the surface of the foot to form an effective light seal, minimizing reflections or light leakage at that interface. The detector 24 also preferably is configured in a similar manner (with a light seal).

Next, at step 1140, some fraction of the light transmitted 38 within the foot naturally reflects back toward the detector 24. This reflection has data that step 1150 uses to determine blood flow characteristics. Some embodiments may use conventional techniques to determine blood flow characteristics, while other embodiments may use proprietary techniques.

Calculation of Cardiovascular Parameters

Among others, cardiac health parameters the platform determines may include heart rate, heart rate variability (e.g., HRV), respiration rate, and oxygen saturation. Post-processing signal processing devices configured with signal processing capabilities can be used to gather heart rate variability which follows calculation of consecutive RR intervals given a photoplethysmography (e.g., PPG) waveform.

Heart rate variability is a metric of interest given the growing elderly population because it calculates the variation in the time interval between consecutive heartbeats. Heart rate variability is a marker for how well one can adapt to environmental and psychological challenges, with elevated values being linked with atrial fibrillation, and lower values linked to coronary artery disease. Establishing a pattern of variability given a patient's history allows for fast diagnosis of cardiac complications.

In addition, calculation of heart rate can also be completed using an algorithm in post-processing devices (e.g., processors using software) that involves peak detection. Irregular heart rate is a strong predictor of arrhythmia and cardiomyopathy. Lastly, respiration rate is a metric from a PPG signal given a set of band pass filtering or other sets of digital filters with varying cutoff frequencies. Increasing respiration rates can be indicative of patient deterioration and respiratory failure.

Information Output

The PPG signal may be output to the user in the form of a summary statistic, such as heart rate, heart rate variability, respiration rate, or blood oxygenation. Alternatively, the waveform can be stored and analyzed offline by a medical professional to diagnose other systemic cardiovascular conditions such as arrhythmias or more local conditions such as peripheral vascular disease.

Figure 12:
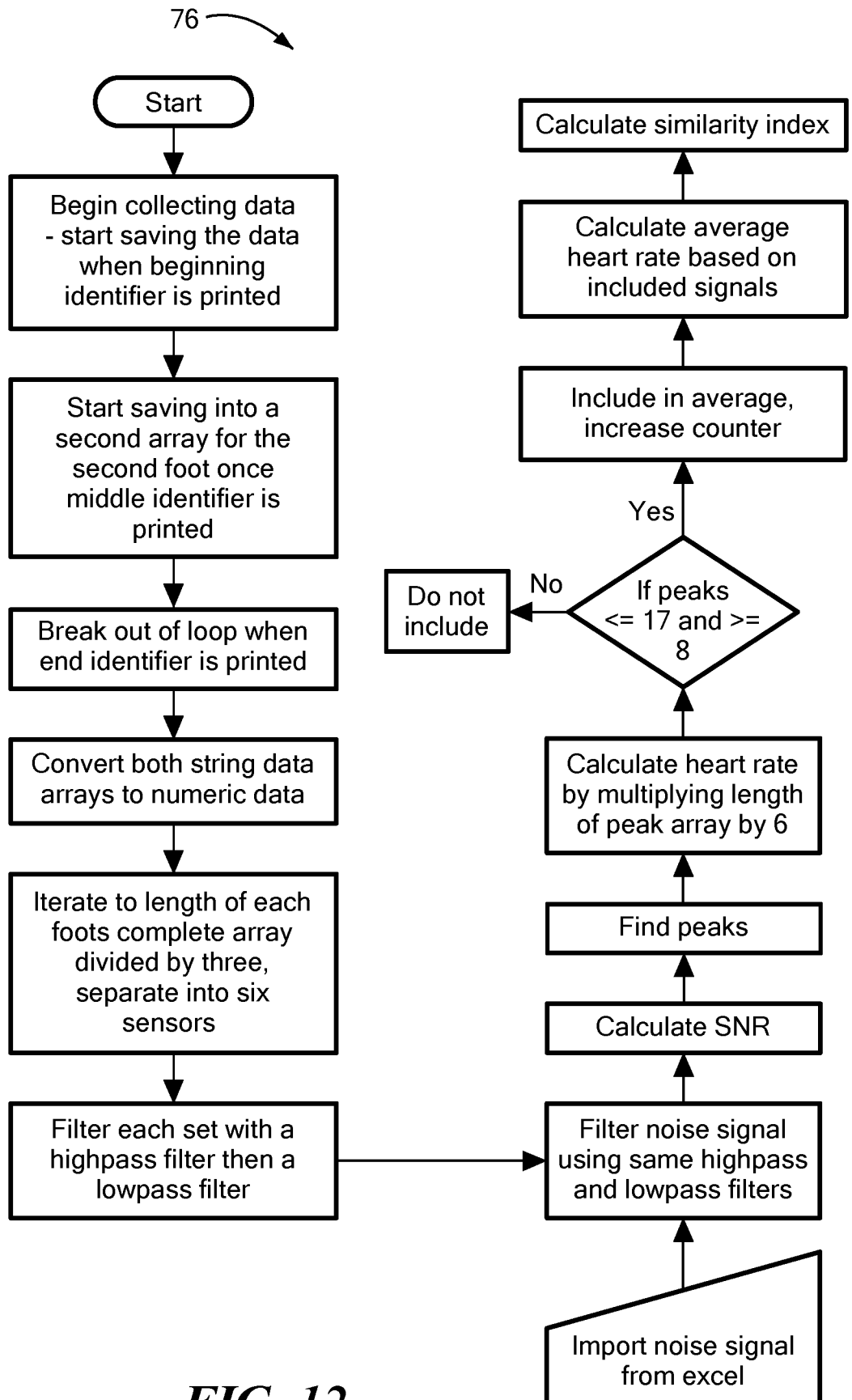
FIG. 12 shows an embodiment of an algorithm to analyze PPG data.
Figure 13:
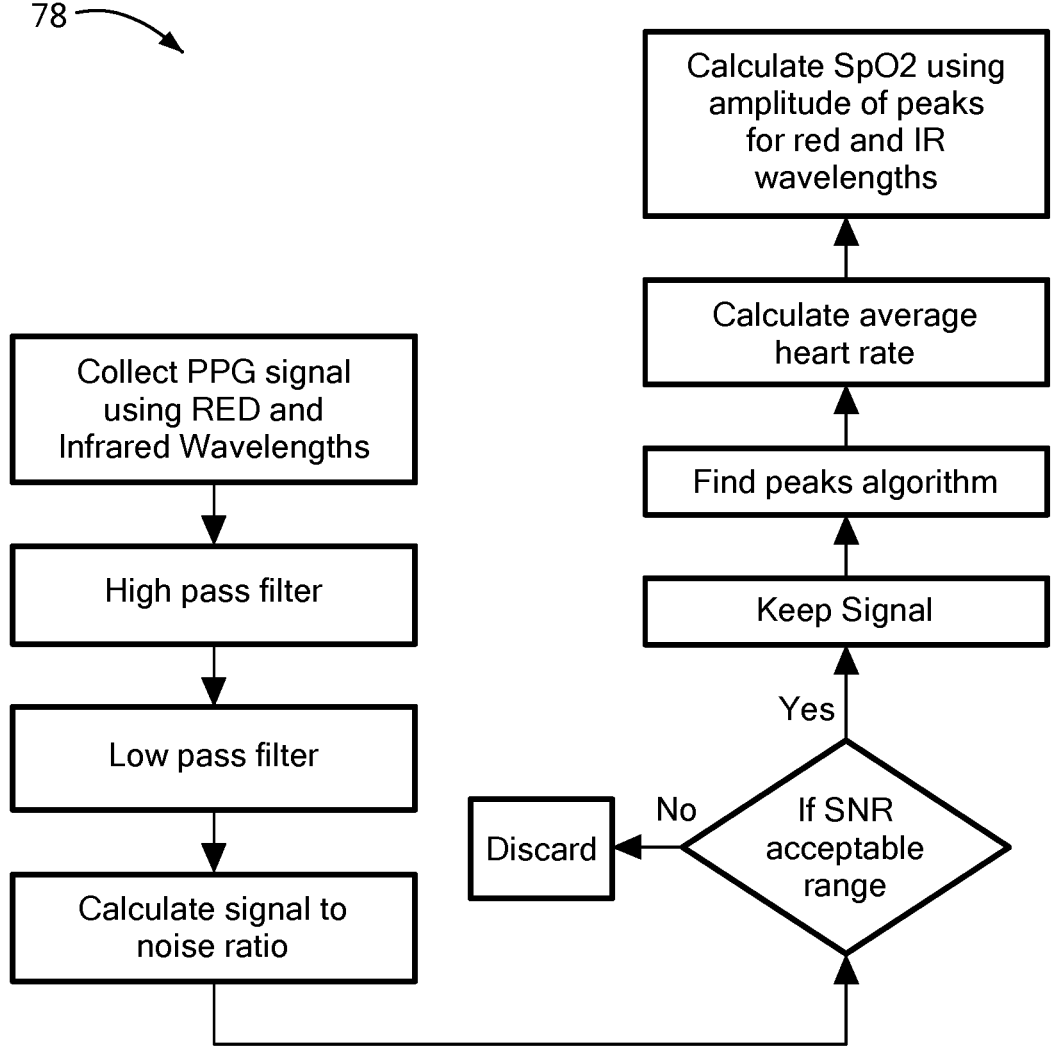
FIG. 13 shows an embodiment of an algorithm to analyze PPG data.
Figure 14:
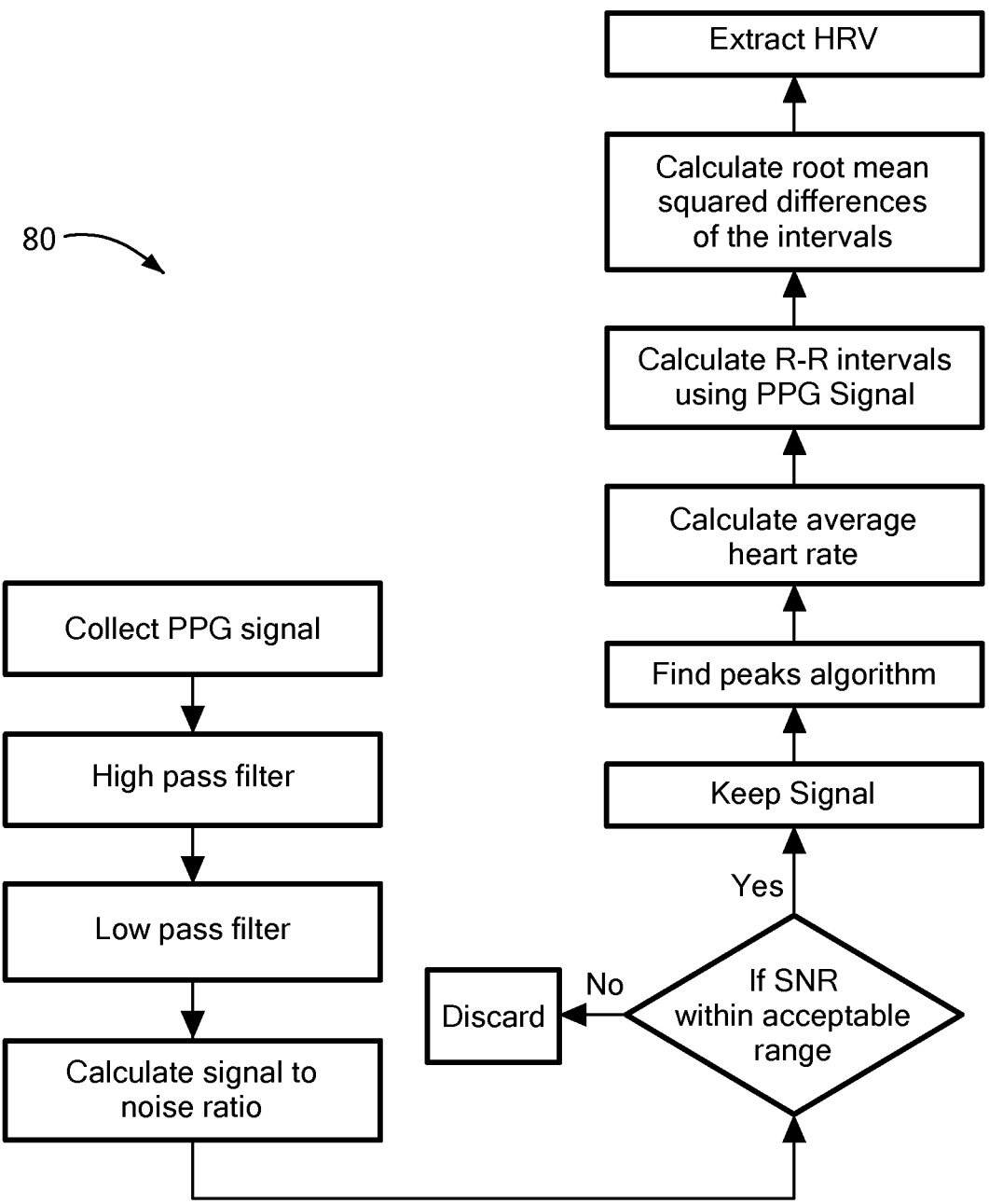
FIG. 14 shows an embodiment of an algorithm to analyze PPG data, FIG. 15A schematically shows an embodiment of an open platform modality that allows one or more PPG measurements to be taken, FIG. 15B schematically shows an embodiment of an open platform modality that allows one or more PPG measurements to be taken, FIG. 16 schematically shows a top view, and two side views of an embodiment of a platform.

FIGS. 12-14 show processes that may be used to implement various embodiments. These processes are not described in detail as those skilled in the art can ascertain how to implement them from the charts themselves. It should be noted that those process are simplified from longer processes. Accordingly, the process may have additional steps that those skilled in the art likely would use. In addition, some of the steps may be performed in a different order than that shown, or at the same time. Those skilled in the art therefore can modify the process and specific parameters as appropriate.

Specifically, FIG. 12 shows an embodiment of an algorithm 76 to analyze PPG data. FIG. 12 shows a "find peaks" technique, which determines whether a certain peak that it finds is valid. In summary, the find peaks technique checks both the amplitude and distance from the previous peak and determines whether or not to include it in the detection process. The algorithm 76 can be adjusted for each amplitude and distance depending on the heart rate and waveform of the signal collected.

Illustrative embodiments also determine a "similarity index," which is indicative of the accuracy of the device in relation to a finger pulse oximeter. Preferably, the similarity index is an output from the device, preferably on a display, although heart rate calculations also may be displayed. In summary, the similarity index is calculated by 1) averaging the heart rates extracted the determined to be in a valid range by the find peaks technique, 2) subtracting that average from a heart rate from the finger, and 3) taking an average. Exemplary logic for the inclusion of certain heart rates is included in a flowchart in FIG. 12.

FIG. 13 shows an embodiment of an algorithm 78 to analyze PPG data to determine SpO₂, also known as "oxygen saturation," which is an important reading for the patient population as it can be indicative of early cardiac decline. The SpO₂ can be gathered from the device by collecting data with red and infrared wavelengths, as shown in FIG. 13. This data will be filtered and sorted a similar manner, but the amplitude of each wavelength compared to each other will provide an oxygen saturation measurement. Oxygen saturation can be calculated as shown below, where RED and IR refer to the wavelength of light being used.

$$S_pO_2 \simeq 110 - 25\left(\frac{\frac{RMS(RED)}{MEAN(RED)}}{\frac{RMS(IR)}{MEAN(IR)}}\right)$$

HRV is another important metric that is often used to determine cardiac health over an extended period of time. FIG. 14 illustrates a flow diagram 80 for the determination of HRV from a PPG signal. Specifically, after calculating the average heart rate, the intervals between each "R" section of the peaks, shown in FIG. 14, may be calculated. The length of these intervals is then averaged and used to calculate a root mean squared of the differences ("RMSSD"). After the RMSSD is calculated, heart rate variability can be extracted.

EXAMPLES

The following examples are intended to further illustrate illustrative embodiments.

Example 1: PPG Apparatus Prototype

Figure 15A:
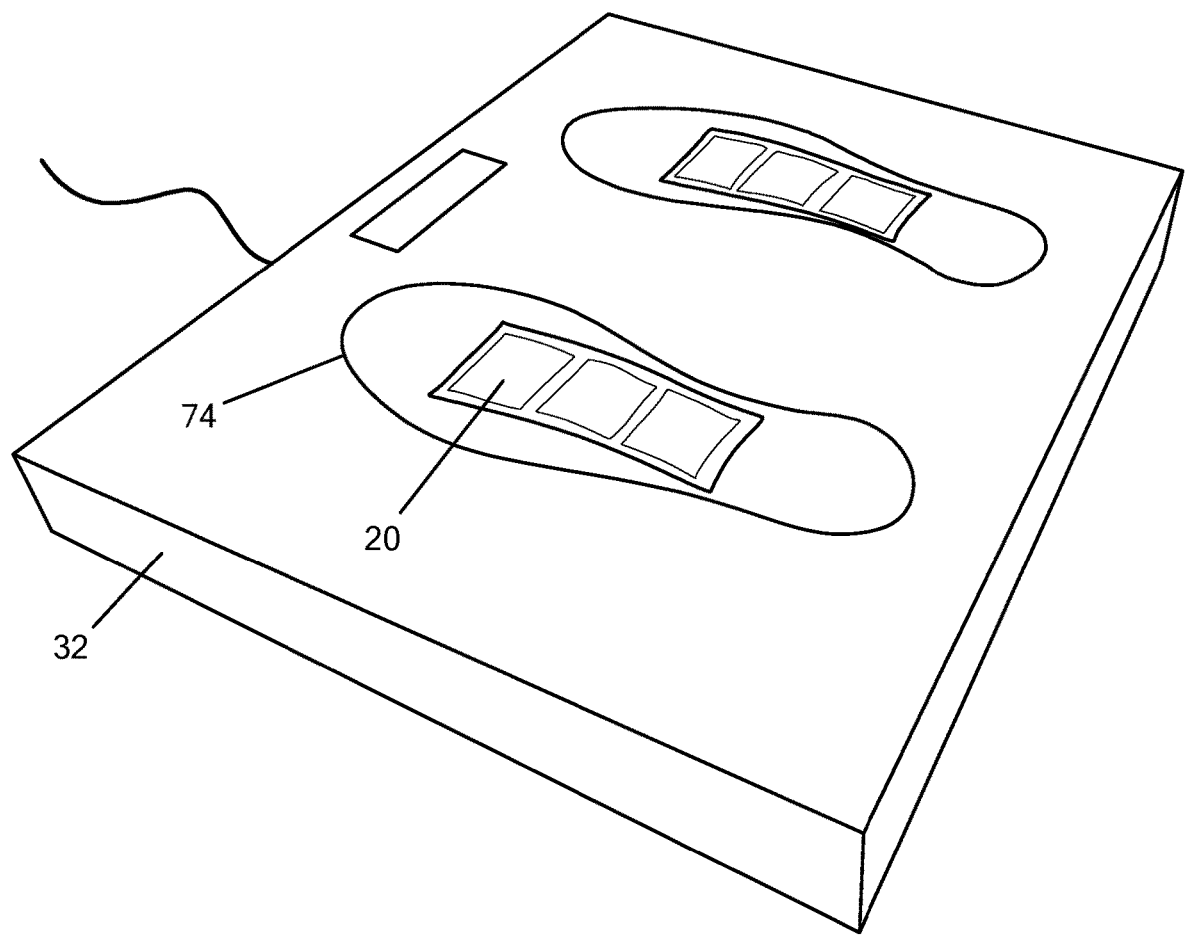

A prototype apparatus for measuring blood flow in feet with PPG sets was constructed. To that end, FIG. 15A shows a picture of an embodiment of an open platform modality 16 that allows one or more photoplethysmography ("PPG") measurements to be taken from the plantar surfaces of the feet of patients. This prototype uses two 1×3 arrays of LED-photodetector pair sensors (e.g., PPG sets 20) mounted in the rigid platform 16. Guide indicia 74 are indicated on the top surface 14 of the cover to direct where the patient communicates his/her foot/feet 10 with the platform 16 (e.g., stepping on the noted open platform).

Figure 15B:
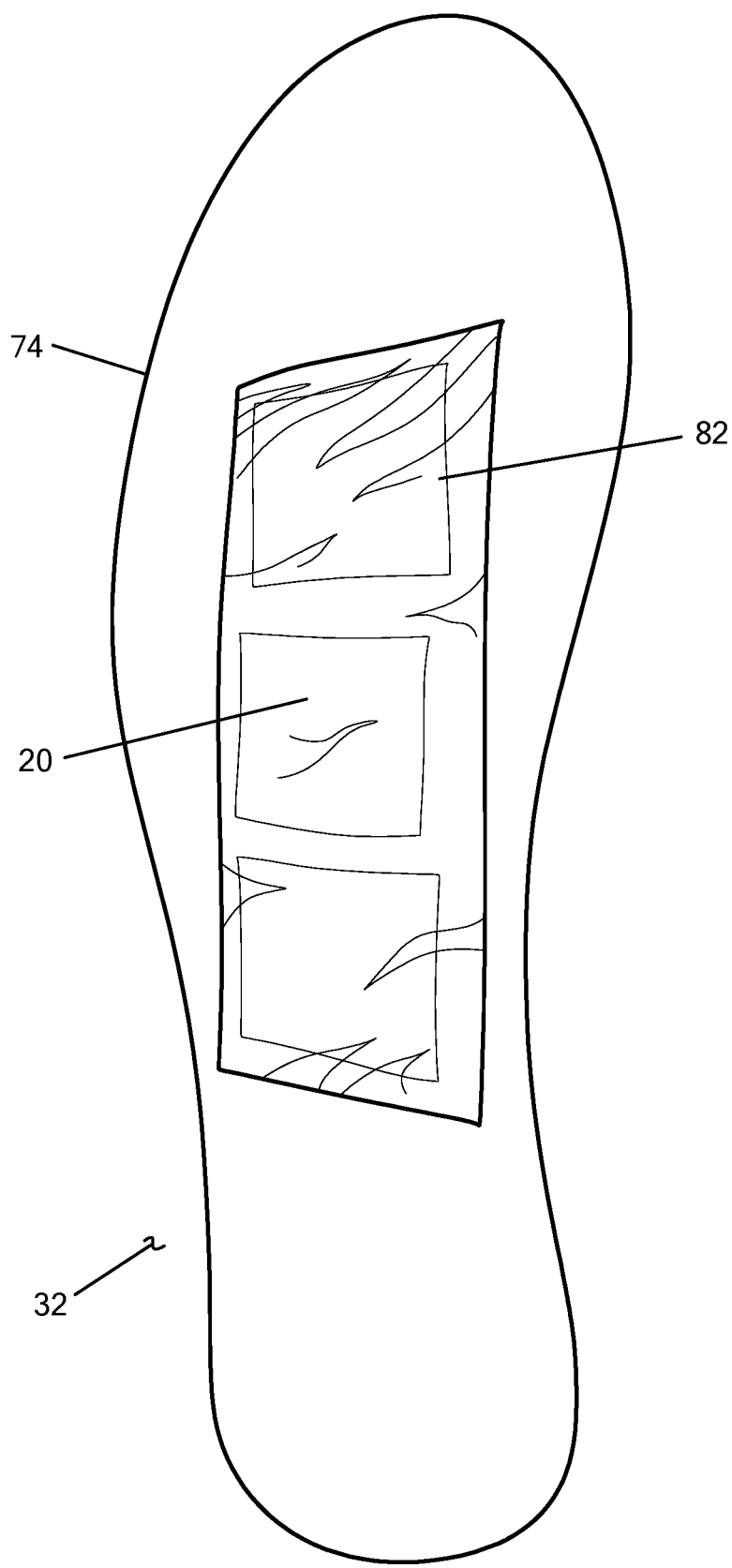

FIG. 15B shows an expanded view of the left 1×3 array of FIG. 15A. The PPG sets 20 are housed in PPG casings 28, as shown in FIG. 16A, and connected to springs. The top view of PPG casing 28 shown in FIG. 16A illustrates the placement of the PPG set 20 as shown in FIG. 15B. Each of the PPG sets 20 are be placed into a designed cover for protection from the environment and from the foot 10, with a hole for an LED 22 and a hole for a photodetector 24. The LED-photodetector casing 28 (e.g., PPG set casing) is made from a thermoplastic polyurethane. These casings 28 provide structural and waterproofing protection to the electrical LEDs 22 and photodetectors 24, while providing adequate space for soldered-on electrical wiring. Furthermore, the casings 28 allow the LED-photodetector combination 20 (e.g., PPG sets) to protrude above flush of the cover 14 thickness to facilitate contact with the feet and the production and detection signals. The encased PPG sets 20 and springs 26 are mounted to a base (e.g., a waterproof base) that houses the electronics. To minimize accidents, the base has anti-slip materials on the bottom surface.

The PPG sets 20 are preprogrammed to have specific brightness settings and sampling frequencies. The springs 26 control the force of contact between the PPG sets 20 and plantar surfaces of the foot 10. A film 82 transparent at specific wavelengths (e.g., visible light wavelengths or IR wavelengths) at least in part covers the PPG sets 20 and acts as the interface between the PPG sets 20 and the feet 10, as shown in FIGS. 15A and 15B.

Figure 16:
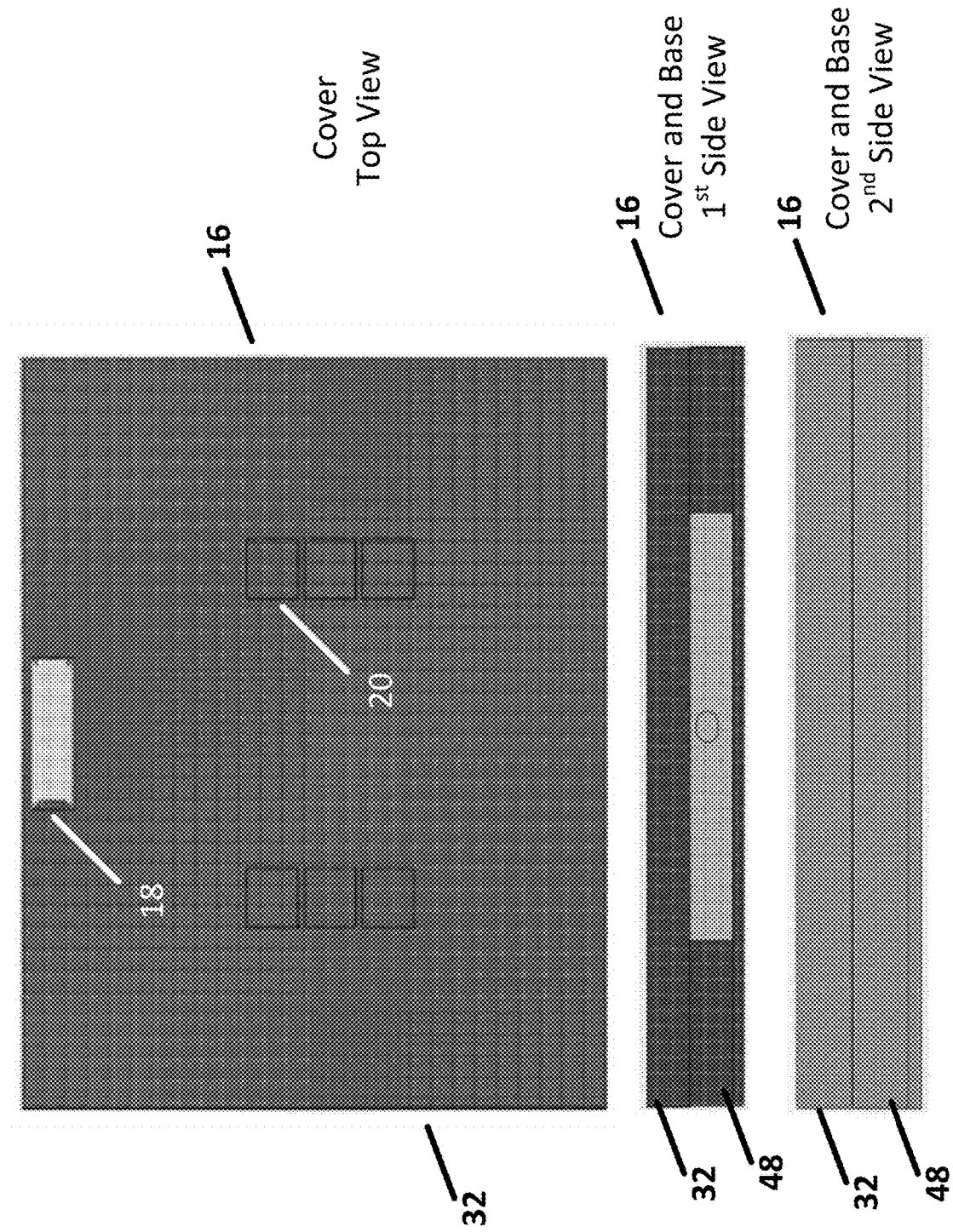
Figure 17:
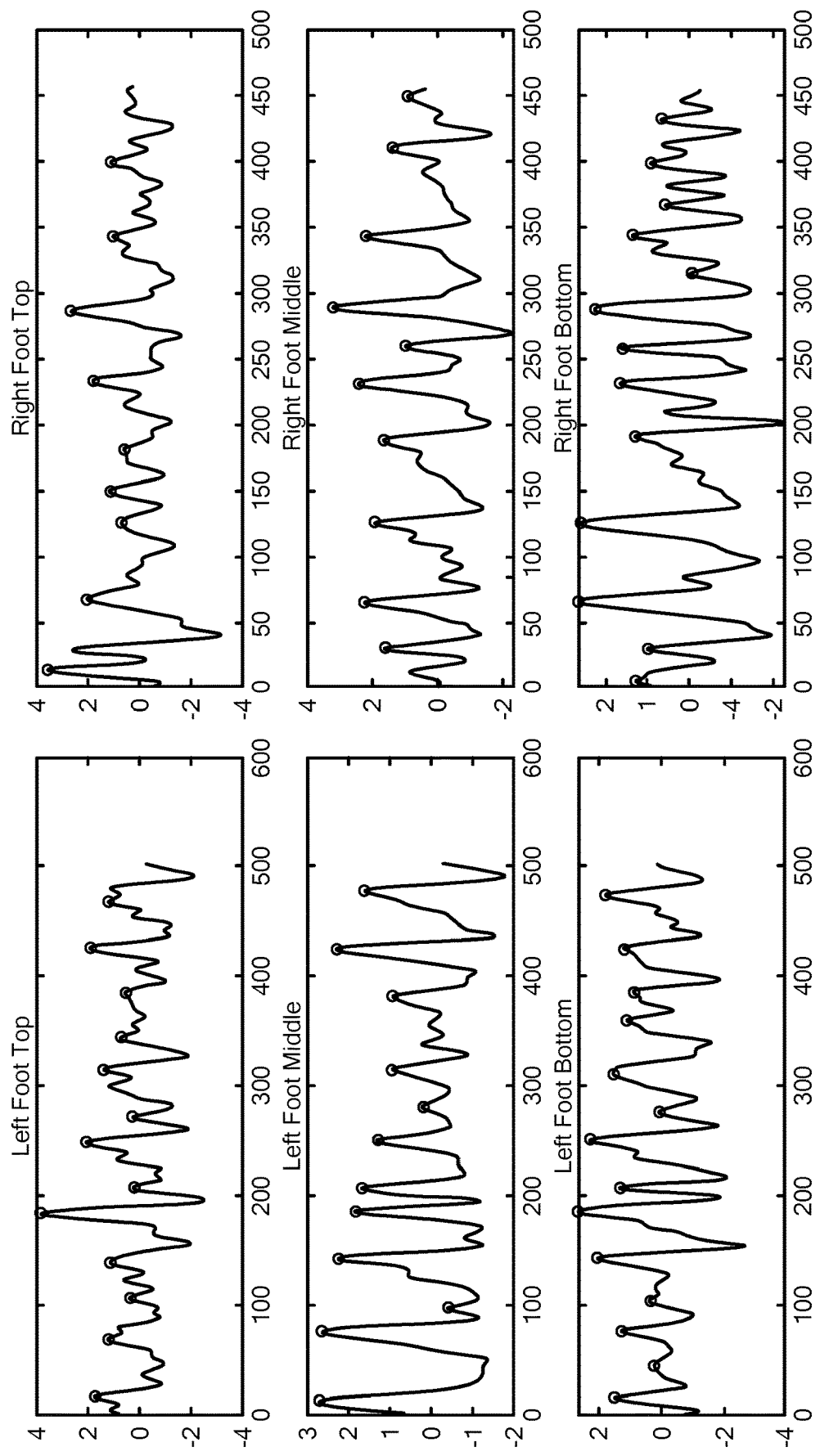
FIG. 17 shows the final peaks found for three sets of PPG data (top, middle, and bottom) for each foot after processing the filtered data.

The rigid platform 16 is further illustrated in FIG. 16. A top view of the cover 32 of the platform 16 is shown with the two 1×3 arrays of PPG sets 20. Two side views of the platform 16 showing the cover 32 and the base 48 are also shown in FIG. 17.

The platform 16 provides an inner housing that fully encloses all electronics components and includes cutouts for each of the following: battery, power switch, microcontroller, sensor, wires, pressure sensor, and LED strip for an interface screen. A prototype apparatus was used to take PPG measurements from the photodetector-LED sensors in the array(s), and record those readings in memory. A data file containing the recorded data was transmitted to a remote processor. The data was analyzed using data with signal processing and filtering functionality, as well as with a process to calculate heart rate and signal-to-noise ratio. These and other details are discussed in more detail below.

After receipt by the processing device, the raw data was filtered using a combination of a high-pass and low-pass digital filters operating at prescribed, different cutoff frequencies and within the frequency range for detectable photoplethysmography waveforms, as described above for FIGS. 12-14. There are multiple ways to filter the data so that heart rate and other metrics can be determined from the waveforms; the combination filtering discussed below is one exemplary method.

Heart rate is an informative metric that the inventors recognized may be acquired from the PPG waveform for the purposes of internal validation of the device. Calculation of heart rate involves an automated peak detection algorithm that can be implemented using a variety of formulations in which peaks of certain amplitude are marked as being of interest. The peaks from this detection algorithm are then utilized to extract a heart rate over a time course determined by the time of interest and total time spent.

Another way to verify the value of the signal is determining the signal-to-noise ratio, which can be calculated by utilizing a pre-programmed signal to noise ratio function in post-processing software. There are multiple other ways to calculate a signal to noise ratio, including calculating the power in both a signal and a noise reading, or taking the ratio of the amplitudes of these signals, both of which can be done using a post-processing or analytic software with some level of signal processing capabilities.

The prototype apparatus shown in FIGS. 15A and 15B was utilized to take PPG measurements. As shown in FIGS. 15A and 15B, the apparatus has two 1×3 arrays with top, middle, and bottom PPG sets for each foot. The data sets measured therefore have three sets of PPG data for each foot.

PPG Measurements and Data Processing

The process of FIG. 12 is effective at finding peaks in raw PPG set data that can be used to generate information about blood flow in a person's foot. It is important to note that using the process of FIG. 12, during testing, even the poor data was able to be filtered, and peaks were able to be detected so that heart rate could be extracted.

FIG. 17 shows final peaks found for three sets of PPG data (top, middle, and bottom) for each foot after processing the filtered data. By using the "find peaks" algorithm 76 of FIG. 12 with the filtered data, it was possible to find the peaks necessary to calculate s similarity index. This is notable because the initial data was of poor quality.

Various embodiments of the invention may be implemented at least in part in any conventional computer programming language. For example, some embodiments may be implemented in a procedural programming language (e.g., "C"), or in an object oriented programming language (e.g., "C++"). Other embodiments of the invention may be implemented as a pre-configured, stand-alone hardware element and/or as preprogrammed hardware elements (e.g., application specific integrated circuits, FPGAs, and digital signal processors), or other related components.

In an alternative embodiment, the disclosed apparatus and methods (e.g., see the various flow charts described above) may be implemented as a computer program product for use with a computer system. Such implementation may include a series of computer instructions fixed either on a tangible, non-transitory medium, such as a computer readable medium (e.g., a diskette, CD-ROM, ROM, or fixed disk). The series of computer instructions can embody all or part of the functionality previously described herein with respect to the system.

Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies.

Among other ways, such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). In fact, some embodiments may be implemented in a software-as-a-service model ("SAAS") or cloud computing model. Of course, some embodiments of the invention may be implemented as a combination of both software (e.g., a computer program product) and hardware. Still other embodiments of the invention are implemented as entirely hardware, or entirely software.

The embodiments of the invention described above are intended to be merely exemplary; numerous variations and modifications will be apparent to those skilled in the art. Such variations and modifications are intended to be within the scope of the present invention as defined by any of the appended claims.

What is claimed is:

1. An apparatus for measuring blood flow in a foot, the apparatus comprising:
   a platform having a platform contact surface configured to receive the foot, the platform contact surface configured to receive a foot force having a foot force magnitude when the platform contact surface receives the foot;
   a plurality of PPG sets extending through the platform contact surface, each PPG set having at least one light source and at least one light detector; and
   a plurality of springs,
   each PPG set being coupled with one or more of the plurality of springs,
   each PPG set being movably coupled with the platform by the one or more of the plurality of springs,
   each spring biased to produce a biasing force via its coupled PPG set when the platform contact surface receives the foot,
   each PPG set and its corresponding one or more springs configured so that the biasing force has a biasing force magnitude that is substantially independent of the foot force magnitude.

2. The apparatus as defined by claim 1 wherein the plurality of PPG sets comprises a first PPG set with a first spring with a first spring constant, the plurality of PPG sets also includes a second PPG set with a second spring having a second spring constant, the first spring constant being different from the second spring constant.

3. The apparatus as defined by claim 1 wherein the plurality of PPG sets comprises a first PPG set with a first top contact surface spaced a first distance from the platform contact surface,
   the plurality of PPG sets also includes a second PPG set with a second top contact surface spaced from a second distance from the platform contact surface, the first distance being greater than the second distance.

4. The apparatus as defined by claim 1 wherein the plurality of PPG sets are configured to produce a plurality of different wavelengths of light at the same time.

5. The apparatus as defined by claim 1 wherein each PPG set is constrained to move substantially in one dimension only.

6. The apparatus as defined by claim 1 wherein the platform contact surface comprises a plurality of apertures, each of the plurality of apertures containing at least one of the plurality of PPG sets and at least one of the plurality of springs, each PPG set configured to move substantially normal to the platform surface within the aperture in response receipt of the foot force.

7. The apparatus as defined by claim 1 wherein the platform contact surface comprises a plurality of apertures, each of the plurality of apertures containing at least one of the plurality of PPG sets and at least one of the plurality of springs, each PPG set configured to move not normal to the platform surface within the aperture in response receipt of the foot force.

8. The apparatus as defined by claim 7 wherein each of the plurality of PPG sets has a top contact surface configured to contact the foot, the springs configured to permit the top contact surface to be movable to be substantially flush or below the level of the platform contact surface in response to the foot force.

9. The apparatus as defined by claim 1 wherein the plurality of springs comprises one or more of a coil spring, a leaf spring, cantilever spring, foam spring, viscoelastic spring, and/or an elastomeric spring.

10. The apparatus as defined by claim 1 wherein the at least one light source comprises a light emitting diode and the at least one light detector comprises a photodetector.

11. The apparatus as defined by claim 1 wherein the at least one spring is configured to produce a light seal that prevents leakage of reflective light from the foot at the location of the light source.

12. The apparatus as defined by claim 1 wherein the platform is configured as an open platform.

13. The apparatus as defined by claim 1 wherein the platform is configured as a closed platform.

14. The apparatus as defined by claim 1 wherein the biasing force is configured to range from 1 N to 10 N.

15. The apparatus as defined by claim 1 further comprising guide indicia identifying where to place a foot on the platform.

16. The apparatus as defined by claim 1 further comprising a visual display configured to show measurement status.

17. The apparatus as defined by claim 1 further comprising a placement system configured to start analyzing a foot in response to measurements of at least one PPG set and/or a pressure sensor.

18. The apparatus as defined by claim 1 wherein the plurality of PPG sets comprises a two-dimensional array of PPG sets extending from the platform contact surface.

19. The apparatus as defined by claim 1 wherein each PPG set is configured to form an effective light seal when abutting the foot.

20. An apparatus for measuring blood flow in a foot, the apparatus comprising:
a platform having a platform contact surface configured to receive the foot, the platform contact surface configured to receive a foot force having a foot force magnitude when the platform contact surface receives the foot;
a first PPG set having a first light source configured to emit light at a first wavelength, the first PPG set also having a first light detector, the first PPG set normally extending above the platform contact surface;
a second PPG set having a second light source configured to emit light at a second wavelength, the second PPG set also having a first light detector, the first wavelength and the second wavelength being different, the second PPG set normally extending above the platform contact surface;
a first spring coupled with the first PPG set, the first spring movably coupling the first PPG set with the platform, the first spring biased to produce a first biasing force via the first PPG set when the platform contact surface receives the foot;
a second spring coupled with the second PPG set, the second spring movably coupling the second PPG set with the platform, the second spring biased to produce a second biasing force via the second PPG set when the platform contact surface receives the foot,
the platform contact surface forming a first aperture at least in part containing the first PPG set and the first spring, the platform contact surface forming a second aperture at least in part containing the second PPG set and the second spring, the first PPG set configured to move within and at least in part outside of the first aperture, the second PPG set configured to move within the second aperture and at least in part outside of the second aperture,
the first PPG set and the first spring configured so that the first biasing force has a magnitude substantially independent of the foot force magnitude.

21. The apparatus as defined by claim 20 wherein the first PPG set is configured to emit light at the first wavelength at the same time that the second PPG set emits light at the second wavelength.

22. The apparatus as defined by claim 20 wherein the first spring has a first spring constant, further wherein the second spring comprises a second spring constant, the first spring constant being different from the second spring constant.

23. The apparatus as defined by claim 20 wherein the first PPG set has a first top contact surface spaced a first distance from the platform contact surface of the platform, further wherein the second PPG set has a second top contact surface spaced a second distance from the platform contact surface of the platform,
the first distance being greater than the second distance.

24. The apparatus as defined by claim 20 wherein the first spring comprises one or more of a coil spring, a leaf spring, a cantilever spring, a foam spring, a viscoelastic spring and/or an elastomeric spring.

25. The apparatus as defined by claim 20 wherein the first light source comprises a light emitting diode and first light detector comprises a photodetector.

26. The apparatus as defined by claim 20 wherein the first light source is configured to cause no reflective light to return to the first light detector.

27. The apparatus as defined by claim 20 wherein the platform is configured as an open platform.

28. The apparatus as defined by claim 20 further comprising a visual display configured to show measurement status.

29. The apparatus as defined by claim 20 further comprising a placement system configured to start analyzing a foot in response to measurements of at least the first PPG set or a pressure sensor.

30. The apparatus as defined by claim 20 wherein the first PPG set is configured to contact a portion of the foot not in contact with the platform contact surface when the contact surface of the platform receives the foot.

31. A method of measuring blood flow in a foot, the method comprising:
positioning a foot on a platform having a platform contact surface with a plurality of apertures, the platform having a plurality of PPG sets, each PPG set having at least one light source and at least one light detector and being biased toward the foot through one of the apertures in the platform contact surface, the foot producing a foot force toward the platform contact surface when positioned on the platform contact surface;

producing, by each PPG set, a biasing force with a magnitude substantially independent of the foot force;

directing, by the PPG sets, light into the foot;

receiving, by the PPG sets, reflection of the light directed into the foot; and determining a blood flow characteristic from the received light.

32. The method as defined by claim 31 wherein positioning a foot comprises using guide indicia to position the foot.

33. The method as defined by claim 32 wherein the guide indicia comprises a guide member formed on or by the platform contact surface.

34. The method as defined by claim 31 further comprising displaying measurements of at least one of the plurality of PPG sets on a visual display.

35. The method as defined by claim 31 wherein directing, by the PPG sets, light into the foot comprises directing multiple wavelengths of light into the foot at substantially the same time.

36. The method as defined by claim 31 wherein positioning comprises abutting each PPG set against the foot so that at least one PPG set produces a concavity in the foot.

37. The method as defined by claim 36 wherein at least one PPG set applies a contact force to the concavity sufficient to direct the light into the foot for receipt, the contact force being less than an amount constraining foot blood flow.

38. The method as defined by claim 31 wherein the foot has a non-contact portion that does not contact the platform contact surface when the foot is positioned on the platform contact surface, a first of the plurality of PPG sets contacting the non-contact portion of the foot at a given time, the foot having a contact portion in contact with the platform contact surface when the foot is positioned on the platform contact surface and when the non-contact portion does not contact the platform contact surface, a second of the plurality of PPG sets contacting the contact portion of the foot at the given time.

* * * * *